United States Patent
Arakawa et al.

(10) Patent No.: US 11,497,731 B2
(45) Date of Patent: Nov. 15, 2022

(54) β-LACTAMASE INHIBITOR

(71) Applicant: NATIONAL UNIVERSITY CORPORATION TOKAI NATIONAL HIGHER EDUCATION AND RESEARCH SYSTEM, Aichi (JP)

(72) Inventors: Yoshichika Arakawa, Aichi (JP); Jun-ichi Wachino, Aichi (JP); Kouji Kimura, Aichi (JP); Wan Chun Jin, Aichi (JP); Ayato Sato, Aichi (JP)

(73) Assignee: NATIONAL UNIVERSITY CORPORATION TOKAI NATIONAL HIGHER EDUCATION AND RESEARCH SYSTEM, Aichi (JP)

( * ) Notice: Subject to any disclaimer, the term of this patent is extended or adjusted under 35 U.S.C. 154(b) by 105 days.

(21) Appl. No.: 17/055,006

(22) PCT Filed: May 14, 2019

(86) PCT No.: PCT/JP2019/019133
§ 371 (c)(1),
(2) Date: Nov. 12, 2020

(87) PCT Pub. No.: WO2019/221122
PCT Pub. Date: Nov. 21, 2019

(65) Prior Publication Data
US 2021/0236463 A1  Aug. 5, 2021

(30) Foreign Application Priority Data
May 14, 2018 (JP) .............. JP2018-093369

(51) Int. Cl.
A61K 31/40 (2006.01)
A61P 31/04 (2006.01)
A61K 45/06 (2006.01)
C07D 207/34 (2006.01)
C07D 207/36 (2006.01)

(52) U.S. Cl.
CPC .............. A61K 31/40 (2013.01); A61K 45/06 (2013.01); A61P 31/04 (2018.01); C07D 207/34 (2013.01); C07D 207/36 (2013.01)

(58) Field of Classification Search
CPC ........ C07D 207/34; A61P 31/04; A61K 31/40
See application file for complete search history.

(56) References Cited

U.S. PATENT DOCUMENTS

| 7,541,381 B2 * | 6/2009 | Shoichet .............. C07D 333/34 514/438 |
| 2009/0131394 A1 | 5/2009 | Sutton et al. |
| 2015/0011524 A1 | 1/2015 | Sutton et al. |
| 2015/0073011 A1 | 3/2015 | McGuire et al. |
| 2015/0141401 A1 | 5/2015 | Abe et al. |
| 2016/0024090 A1 | 1/2016 | Abe et al. |
| 2016/0175290 A1 | 6/2016 | McGuire et al. |
| 2016/0362422 A1 | 12/2016 | Sutton et al. |
| 2017/0233393 A1 | 8/2017 | Abe et al. |
| 2017/0327515 A1 | 11/2017 | Sutton et al. |
| 2018/0065989 A1 | 3/2018 | Sutton et al. |
| 2018/0258089 A1 | 9/2018 | Abe et al. |
| 2018/0273549 A1 | 9/2018 | Sutton et al. |
| 2020/0048253 A1 | 2/2020 | Abe et al. |

FOREIGN PATENT DOCUMENTS

| GB | 2533136 | 6/2016 |
| JP | 2015-512440 | 4/2015 |
| JP | 2015-155435 | 8/2015 |
| JP | 2016-520658 | 7/2016 |
| WO | 00/76962 | 12/2000 |
| WO | 2003/070682 | 8/2003 |
| WO | 2012/088283 | 6/2012 |
| WO | 2013/180197 | 12/2013 |
| WO | 2014/198849 | 12/2014 |
| WO | 2016/206101 | 12/2016 |

OTHER PUBLICATIONS

International Search Report dated Jul. 16, 2019 in International (PCT) Application No. PCT/JP2019/019133.
Powers et al., "Structure-Based Discovery of a Novel, Noncovalent Inhibitor of AmpC β-Lactamase", Structure, 2002, vol. 10, pp. 1013-1023.
Extended European Search Report dated Dec. 2, 2021 in European Patent Application No. 19802755.9.
Hsieh, Jui-Hua et al., "Differentiation of AmpC beta-lactamase binders vs. decoys using classification kNN QSAR modeling and application of the QSAR classifier to virtual screening", Journal of Computer-Aided Molecular Design, Mar. 13, 2008, vol. 22, No. 9, pp. 593-609, XP019606737.

* cited by examiner

Primary Examiner — Kamal A Saeed
(74) Attorney, Agent, or Firm — Wenderoth, Lind & Ponack, LLP

(57) ABSTRACT

An object is to provide a compound having β-lactamase inhibitory activity. The object is achieved by a compound represented by formula (1), typified by a compound in which specific positions of a 5-membered ring having planarity are replaced by sulfamoyl and carboxy groups.

13 Claims, 13 Drawing Sheets

IMP-1-compound A
complexd structure
[1.7 Å resolution]

*VIM-2*-compound A
*complexed structure*
[1.5 Å resolution]

NDM-1-compound A
complexed structure
[1.4 Å resolution]

NDM-1-compound I
complexed structure
[1.8 Å resolution]

β-LACTAMASE INHIBITOR

TECHNICAL FIELD

The present invention relates to a β-lactamase inhibitor and the like.

BACKGROUND ART

Bacterial infections are usually treated by bacteriostasis of the causative bacteria or killing the causative bacteria by the action of an antimicrobial drug. However, the use of an antimicrobial drug leads to the emergence of bacteria that are resistant to the antimicrobial drug. For example, for β-lactam antimicrobial drugs, there are resistant bacteria that produce enzymes (β-lactamases) having the activity of decomposing the β-lactam antimicrobial drugs. β-Lactam antimicrobial drugs with a new structure have thus far been developed and used against newly emerging β-lactamase-producing bacteria. Under such circumstances, carbapenem antimicrobial drugs are used as the newest β-lactam antimicrobial drugs.

However, the use of carbapenem antimicrobial drugs results in the emergence of resistant bacteria that produce enzymes (class B β-lactamases and metallo-β-lactamases) having the activity of decomposing the antimicrobial drugs, which poses a problem. These resistant bacteria are resistant to many β-lactam antimicrobial drugs including carbapenem antimicrobial drugs.

One effective countermeasure against bacteria resistant to β-lactam antimicrobial drugs is to use an inhibitor of β-lactamase, which is an enzyme responsible for the resistance mechanism of the resistant bacteria, in combination with an appropriate β-lactam antimicrobial drug (Patent Literature 1 to Patent Literature 3). However, clinically available inhibitors for class B β-lactamases have not been put into practical use.

CITATION LIST

Patent Literature

PTL 1: JP2015-155435A
PTL 2: WO2013/180197
PTL 3: JP2015-512440A

SUMMARY OF INVENTION

Technical Problem

An object of the present invention is to provide a compound having β-lactamase inhibitory activity. Preferably, an object of the present invention is to provide a compound having class B β-lactamase inhibitory activity.

Solution to Problem

The present inventors conducted extensive research to achieve the above objects. They found that a compound represented by formula (1), typified by a compound in which specific positions of a 5-membered ring having planarity are replaced by sulfamoyl and carboxy groups, has β-lactamase inhibitory activity; in particular, class B β-lactamase inhibitory activity. The present inventors conducted further research based on this finding, thus accomplishing the present invention. Specifically, the present invention includes the following embodiments.

Item 1. A β-lactamase inhibitor comprising a compound represented by formula (1) or a salt, hydrate, or solvate thereof,

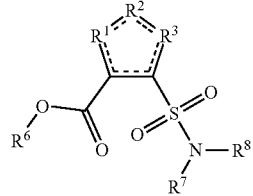

(1)

wherein
$R^1$ represents —C(—$R^A$)—;
$R^2$ represents —N(—$R^B$)$_n$—, —O—, or —C(—$R^A$)—;
$R^3$ represents —C(—$R^A$)— when $R^2$ is —N(—$R^B$)$_n$— or —O—, or represents —S— when $R^2$ is —C(—$R^A$)—;
each $R^A$ is the same or different and represents a hydrogen atom, a halogen atom, or a hydrocarbon group optionally substituted with one or more amino groups;
$R^B$ represents a hydrogen atom, a halogen atom, an optionally substituted amino group, or a hydrocarbon group optionally substituted with one or more amino groups;
n represents 0 or 1;
$R^6$ represents a hydrogen atom or a hydrocarbon group;
$R^7$ and $R^8$ are the same or different and each represents a hydrogen atom or a hydrocarbon group, or $R^7$ and $R^8$ are bonded to each other to form a ring with the adjacent nitrogen atom; and
a bond represented by a double line composed of a solid line and a dotted line is a single bond or a double bond.

Item 2. The inhibitor according to Item 1, wherein the β-lactamase is a class B β-lactamase.

Item 3. The inhibitor according to Item 1 or 2, wherein the β-lactamase is a class B1 β-lactamase.

Item 4. An enhancer of an antimicrobial effect of a β-lactam antimicrobial compound, the enhancer comprising a compound represented by formula (1) or a salt, hydrate, or solvate thereof,

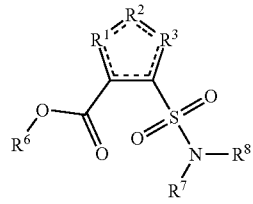

(1)

wherein
$R^1$ represents —C(—$R^A$)—;
$R^2$ represents —N(—$R^B$)$_n$—, —O—, or —C(—$R^A$)—;
$R^3$ represents —C(—$R^A$)— when $R^2$ is —N(—$R^B$)$_n$— or —O—, or represents —S— when $R^2$ is —C(—$R^A$)—;
each $R^A$ is the same or different and represents a hydrogen atom, a halogen atom, or a hydrocarbon group optionally substituted with one or more amino groups;
$R^B$ represents a hydrogen atom, a halogen atom, an optionally substituted amino group, or a hydrocarbon group optionally substituted with one or more amino groups;

n represents 0 or 1;

$R^6$ represents a hydrogen atom or a hydrocarbon group;

$R^7$ and $R^8$ are the same or different and each represents a hydrogen atom or a hydrocarbon group, or $R^7$ and $R^8$ are bonded to each other to form a ring with the adjacent nitrogen atom; and a bond represented by a double line composed of a solid line and a dotted line is a single bond or a double bond.

Item 5. An antimicrobial agent comprising a compound represented by formula (1) or a salt, hydrate, or solvate thereof, and a β-lactam antimicrobial compound,

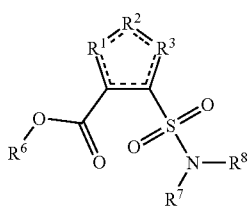

(1)

wherein $R^1$ represents —C(—$R^A$)—;

$R^2$ represents —N(—$R^B$)$_n$—, —O—, or —C(—$R^B$)—;

$R^3$ represents —C(—$R^A$)— when $R^2$ is —N(—$R^B$)$_n$— or —O—, or represents —S— when $R^2$ is —C(—$R^A$)—;

each $R^A$ is the same or different and represents a hydrogen atom, a halogen atom, or a hydrocarbon group optionally substituted with one or more amino groups;

$R^B$ represents a hydrogen atom, a halogen atom, an optionally substituted amino group, or a hydrocarbon group optionally substituted with one or more amino groups;

n represents 0 or 1;

$R^6$ represents a hydrogen atom or a hydrocarbon group;

$R^7$ and $R^8$ are the same or different and each represents a hydrogen atom or a hydrocarbon group, or $R^7$ and $R^8$ are bonded to each other to form a ring with the adjacent nitrogen atom; and a bond represented by a double line composed of a solid line and a dotted line is a single bond or a double bond.

Item 6. An antimicrobial agent comprising a β-lactam antimicrobial compound, the antimicrobial agent being for use in administration in combination with a compound represented by formula (1) or a salt, hydrate, or solvate thereof,

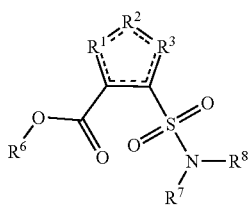

(1)

wherein $R^1$ represents —C(—$R^A$)—;

$R^2$ represents —N(—$R^B$)$_n$—, —O—, or —C(—$R^B$)—;

$R^3$ represents —C(—$R^A$)— when $R^2$ is —N(—$R^B$)$_n$— or —O—, or represents —S— when $R^2$ is —C(—$R^A$)—;

each $R^A$ is the same or different and represents a hydrogen atom, a halogen atom, or a hydrocarbon group optionally substituted with one or more amino groups;

$R^B$ represents a hydrogen atom, a halogen atom, an optionally substituted amino group, or a hydrocarbon group optionally substituted with one or more amino groups;

n represents 0 or 1;

$R^6$ represents a hydrogen atom or a hydrocarbon group;

$R^7$ and $R^8$ are the same or different and each represents a hydrogen atom or a hydrocarbon group, or $R^7$ and $R^8$ are bonded to each other to form a ring with the adjacent nitrogen atom; and a bond represented by a double line composed of a solid line and a dotted line is a single bond or a double bond.

Item 7. A compound represented by formula (1A) or a salt, hydrate, or solvate thereof,

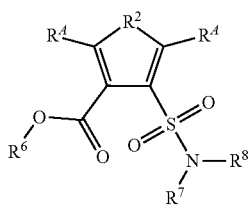

(1A)

wherein $R^2$ represents —N(—$R^B$)— or —O—;

each $R^A$ is the same or different and represents a hydrogen atom, a linear or branched alkyl group optionally substituted with one or more amino groups (with the proviso that when $R^2$ is —N(—$R^B$)—, the alkyl group has 1 to 5 carbon atoms, and when $R^2$ is —O—, the alkyl group has 2 to 5 carbon atoms), a $C_{3-7}$ cyclic alkyl group optionally substituted with one or more amino groups, or a phenyl group optionally substituted with one or more amino groups;

$R^B$ represents a hydrogen atom, an amino group optionally substituted with one or more linear or branched alkyl groups, or an alkyl group optionally substituted with one or more amino groups;

$R^6$ represents a hydrogen atom; and $R^7$ and $R^8$ are the same or different and each represents a hydrogen atom or an alkyl group (with the proviso that the case in which both $R^7$ and $R^8$ are alkyl groups is excluded), or $R^7$ and $R^8$ are bonded to each other to form a ring with the adjacent nitrogen atom.

Item 8. The compound or a salt, hydrate, or solvate thereof according to Item 7, wherein the alkyl group represented by $R^B$ is a $C_{1-4}$ linear alkyl group.

Item 9. A medicament comprising the compound or a salt, hydrate, or solvate thereof according to Item 7 or 8.

Item 10. A reagent comprising the compound or a salt, hydrate, or solvate thereof according to Item 7 or 8.

Advantageous Effects of Invention

The present invention can provide a compound having β-lactamase inhibitory activity, in particular, class B β-lactamase inhibitory activity. By using this compound, an existing β-lactamase inhibitor having a β-lactam ring, an enhancer of the antimicrobial effect of a β-lactam antimicrobial compound, and the like can be provided. Moreover, since the compound of the present invention has relatively low toxicity, the compound can be used more safely.

DESCRIPTION OF EMBODIMENTS

Figure 1:
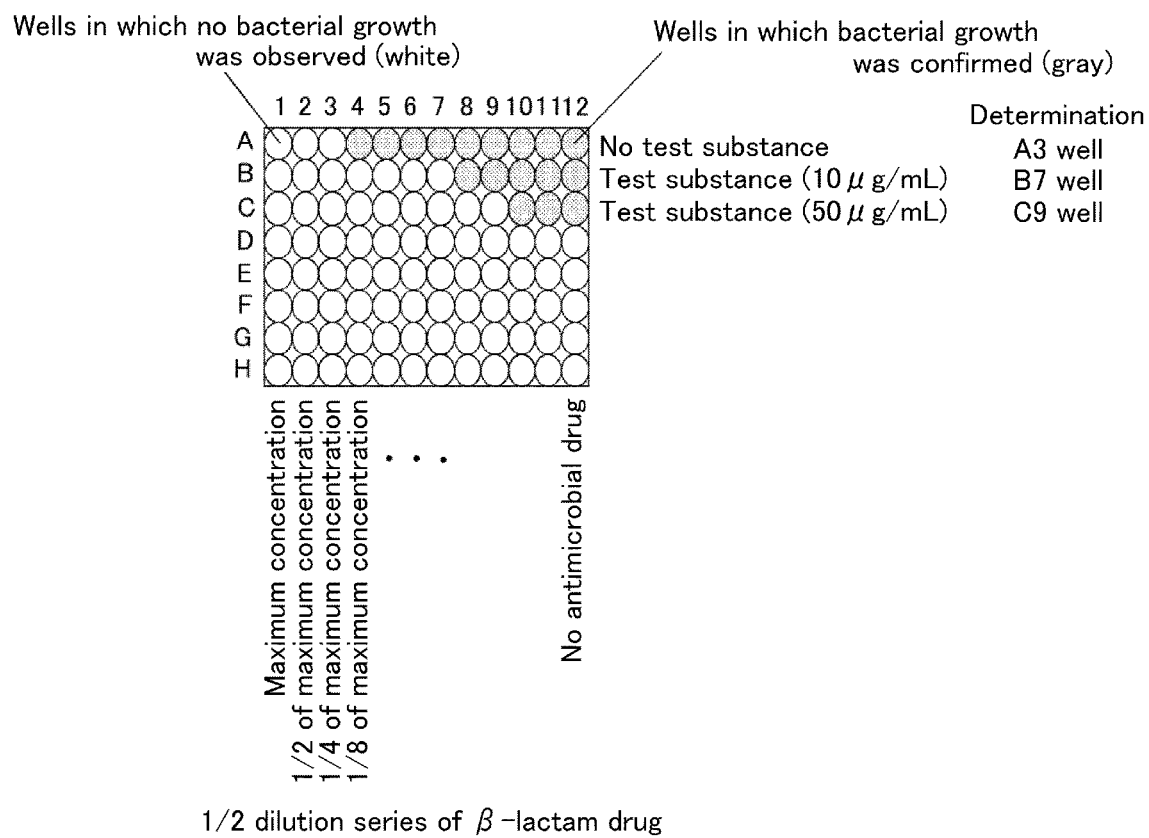
FIG. 1 shows an overview of a test method for a drug susceptibility test (Test Example 1 and the like).

In the present specification, the terms "comprise" and "contain" include the concepts of "comprise," "contain," "consist essentially of," and "consist of."

1. Compound

In one embodiment, the present invention relates to a compound represented by formula (1) or a salt, hydrate, or solvate thereof (in the present specification, these may be referred to as "the compound of the present invention").

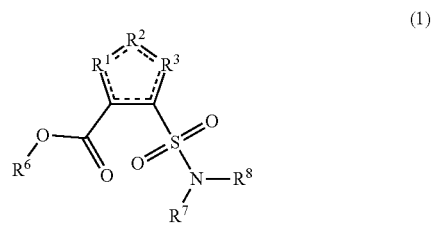

(1)

The compound of the present invention is described below.

1-1. $R^1$, $R^2$, and $R^3$ $R^1$ represents $-C(-R^4)=$. $R^2$ represents $-N(-R^B)_n-$, $-O-$, or $-C(-R^4)=$. $R^3$ represents $-C(-R^4)=$ when $R^2$ is $-N(-R^B)_n-$ or $-O-$, or represents $-S-$ when $R^2$ is $-C(-R^4)=$. $R^2$ is preferably $-N(-R^B)_n-$.

Each $R^4$ is the same or different and represents a hydrogen atom, a halogen atom, or a hydrocarbon group optionally substituted with one or more amino groups. In an embodiment of the present invention, $R^4$ is preferably a hydrocarbon group.

Examples of the halogen atom represented by $R^4$ include fluorine, chlorine, bromine, iodine, and the like.

The hydrocarbon group represented by $R^4$ is not particularly limited. Examples of the hydrocarbon group represented by $R^4$ include alkyl, aryl, and the like; and further include groups composed of any combination of these groups (e.g., aralkyl, alkylaryl, and alkylaralkyl), and the like. In an embodiment of the present invention, the hydrocarbon group is preferably an alkyl group or aryl group. In this embodiment, when there are two $R^4$, the case in which the two $R^4$ are both aryl groups is preferably excluded. The alkyl group represented by $R^4$ includes linear, branched, or cyclic (preferably linear or branched, and more preferably linear) alkyl groups. The number of carbon atoms in the alkyl group (when it is a linear or branched alkyl group) is not particularly limited; and is, for example, 1 to 12, preferably 1 to 8, more preferably 1 to 5, even more preferably 1 to 4, and still even more preferably 1 to 2. The number of carbon atoms in the alkyl group (when it is a cyclic alkyl group) is not particularly limited; and is, for example, 3 to 7, and preferably 4 to 6. In an embodiment of the present invention, the lower limit of the number of carbon atoms in the alkyl group is, for example, 2, 3, 4, 5, 6, 7, or 8. Specific examples of the alkyl group include methyl, ethyl, n-propyl, isopropyl, n-butyl, isobutyl, tert-butyl, sec-butyl, n-pentyl, neopentyl, n-hexyl, 3-methylpentyl, n-heptyl, n-octyl, n-nonyl, n-decyl, n-undecyl, n-dodecyl, and the like.

The aryl group represented by $R^4$ is not particularly limited; and is preferably a $C_{6-12}$ aryl group, more preferably a $C_{6-12}$ aryl group, and even more preferably a $C_{6-8}$ aryl group. The aryl group can be monocyclic or polycyclic (e.g., bicyclic or tricyclic), and is preferably monocyclic. Specific examples of the aryl group include phenyl, naphthyl, biphenyl, pentalenyl, indenyl, anthracenyl, tetracenyl, pentacenyl, pyrenyl, perylenyl, fluorenyl, phenanthryl, and the like. The aryl group is preferably, for example, phenyl.

The aralkyl group represented by $R^A$ is not particularly limited. Examples include aralkyl groups in which one or more hydrogen atoms (for example, one to three hydrogen atoms, preferably one hydrogen atom) of a $C_{1-6}$ (preferably $C_{1-2}$) linear or branched alkyl group are replaced by one or more aryl group described above; and the like. Specific examples of the aralkyl group include benzyl, phenethyl, and the like.

The alkylaryl group represented by $R^A$ is not particularly limited. Examples include alkylaryl groups in which one or more hydrogen atoms (for example, one to three hydrogen atoms, preferably one hydrogen atom) of an aryl described above are replaced by one or more $C_{1-6}$ (preferably $C_{1-2}$) linear or branched alkyl groups; and the like. Specific examples of the alkylaryl group include tolyl, xylyl, and the like.

The alkylaralkyl group represented by $R^A$ is not particularly limited. Examples include alkylaralkyl groups in which one or more hydrogen atoms (for example, one to three hydrogen atoms, preferably one hydrogen atom) on one or more aromatic rings of an aralkyl group described above are replaced by one or more $C_{1-6}$ (preferably $C_{1-2}$) linear or branched alkyl groups; and the like.

When the hydrocarbon group represented by $R^A$ is substituted with an amino group, the amino group encompasses not only —$NH_2$, but also a substituted amino group in which the hydrogen atom(s) of —$NH_2$ are replaced by hydrocarbon group(s). The hydrocarbon group(s) in the substituted amino group are the same as those represented by $R^A$.

$R^B$ represents a hydrogen atom, a halogen atom, an optionally substituted amino group, or a hydrocarbon group optionally substituted with one or more amino groups. In an embodiment of the present invention, $R^B$ is preferably a hydrogen atom or a hydrocarbon group, and more preferably a hydrocarbon group. The halogen atom represented by $R^B$ and the hydrocarbon group optionally substituted with one or more amino groups represented by $R^B$ are the same as those described above for $R^A$.

Examples of the optionally substituted amino group represented by $R^B$ include —$NH_2$; substituted amino groups in which the hydrogen atom(s) of —$NH_2$ are replaced by hydrocarbon group(s); and the like. The hydrocarbon group(s) are the same as those represented by $R^A$.

n represents 0 or 1. In an embodiment of the present invention, n is preferably 1.

1-2. 5-Membered Ring

In formula (1), a bond represented by a double line composed of a solid line and a dotted line is a single bond or a double bond. There is no particular limitation on the 5-membered ring containing the bonds in a partial structure represented by formula (A) in formula (1):

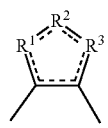

wherein $R^1$, $R^2$, and $R^3$ are the same as above. The 5-membered ring preferably has planarity. Specific examples of the 5-membered ring include furan, pyrrole, thiophene, and the like. The 5-membered ring is more preferably, for example, furan, pyrrole, or the like, and even more preferably, for example, pyrrole.

1-3. $R^6$ $R^6$ represents a hydrogen atom or a hydrocarbon group. In an embodiment of the present invention, $R^6$ is preferably a hydrogen atom. The hydrocarbon group represented by $R^6$ is the same as that described above for $R^A$.

1-4. $R^7$ and $R^8$ $R^7$ and $R^8$ are the same or different and each represents a hydrogen atom or a hydrocarbon group, or $R^7$ and $R^8$ are bonded to each other to form a ring with the adjacent nitrogen atom. In an embodiment of the present invention, it is preferable that $R^7$ and $R^8$ are the same or different and each represents a hydrogen atom or a hydrocarbon group. More preferably, at least one of $R^7$ and $R^8$ is a hydrogen atom. Even more preferably, $R^7$ and $R^8$ are both hydrogen atoms.

The hydrocarbon group represented by $R^7$ and the hydrocarbon group represented by $R^8$ are the same as that described above for $R^A$.

The ring formed by $R^7$ and $R^8$ bonded to each other, together with the adjacent nitrogen atom, is not particularly limited; and is, for example, monocyclic or bicyclic. The ring is, for example, represented by formula (X) or formula (Y):

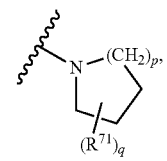

(X)

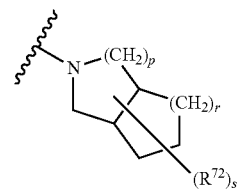

(Y)

wherein $R^{71}$ and $R^{72}$ each represent an alkyl group; p and r each represent an integer of 1 to 3; and q and s each represent 0 or an integer of 1 to 3.

The alkyl group represented by $R^{71}$ and the alkyl group represented by $R^{72}$ are the same as that described above for $R^A$. For each of $R^{71}$ and $R^{72}$, when a plurality of $R^{71}$ is present, they may be bonded to the same carbon atom or different carbon atoms; when a plurality of $R^{72}$ is present, they may be bonded to the same carbon atom or different carbon atoms.

1-5. Preferable Compound of Formula (1)

In one embodiment of the present invention, among formula (1), for example, formula (LA):

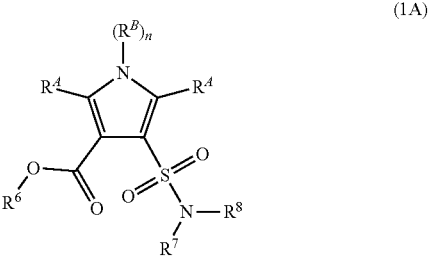

(1A)

wherein $R^A$, $R^B$, n, $R^6$, $R^7$, and $R^8$ are the same as above, is preferable.

In another embodiment of the present invention, among formula (1), for example, formula (1B):

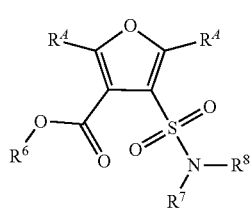
(1B)

wherein $R^A$, $R^6$, $R^7$, and $R^8$ are the same as above, is preferable.

In formulas (1), (LA), and (1B), a preferable embodiment is as follows:

$R^2$ represents —N(—$R^B$)— or —O—;

each $R^A$ are the same or different and represents a hydrogen atom, a linear or branched alkyl group optionally substituted with one or more amino groups (with the proviso that when $R^2$ is —N(—$R^B$)—, the alkyl group has 1 to 5 carbon atoms; and when $R^2$ is —O—, the alkyl group has 2 to 5 carbon atoms), a $C_{3-7}$ cyclic alkyl group optionally substituted with one or more amino groups, or a phenyl group optionally substituted with one or more amino groups; $R^B$ represents a hydrogen atom, an amino group optionally substituted with one or more linear or branched alkyl groups, or an alkyl group optionally substituted with one or more amino groups;

$R^6$ represents a hydrogen atom; and $R^7$ and $R^8$ are the same or different and each represents a hydrogen atom or an alkyl group (with the proviso that the case in which both $R^7$ and $R^8$ are alkyl groups is excluded), or $R^7$ and $R^8$ are bonded to each other to form a ring with the adjacent nitrogen atom.

Specific examples of compounds represented by formula (1) include the following compounds.

Compound A

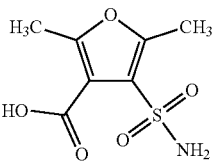

Compound B

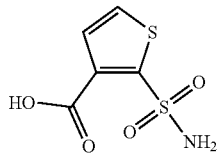

Compound C

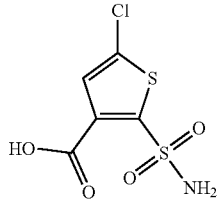

Compound D

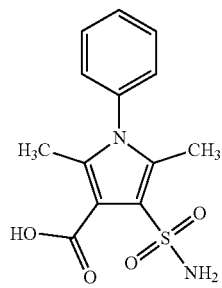

Compound E

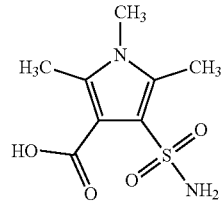

Compound F

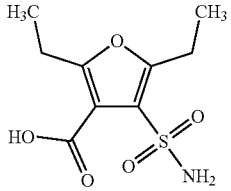

Compound G

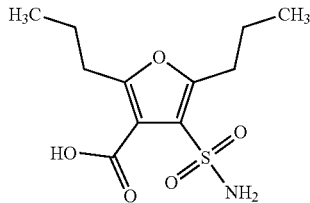

Compound H

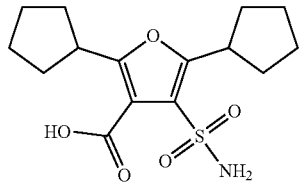

Compound I

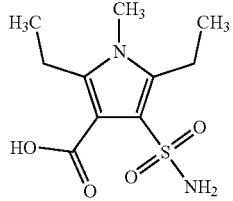

X2a

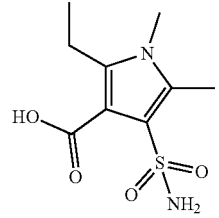

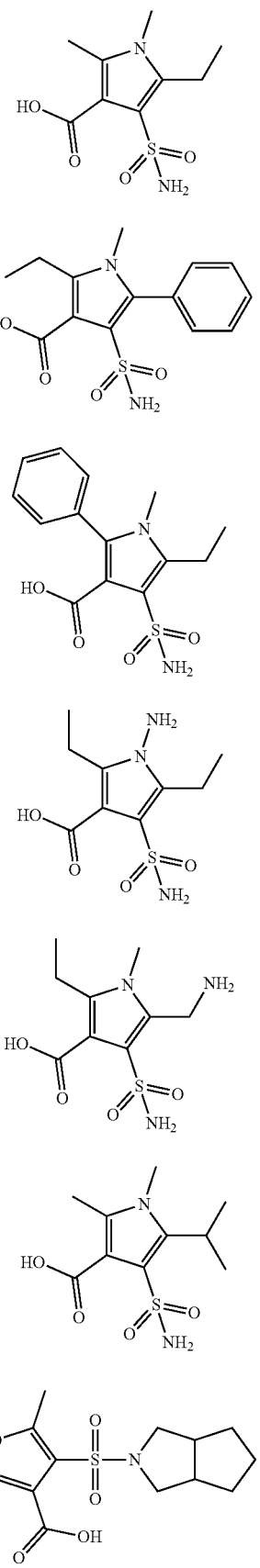

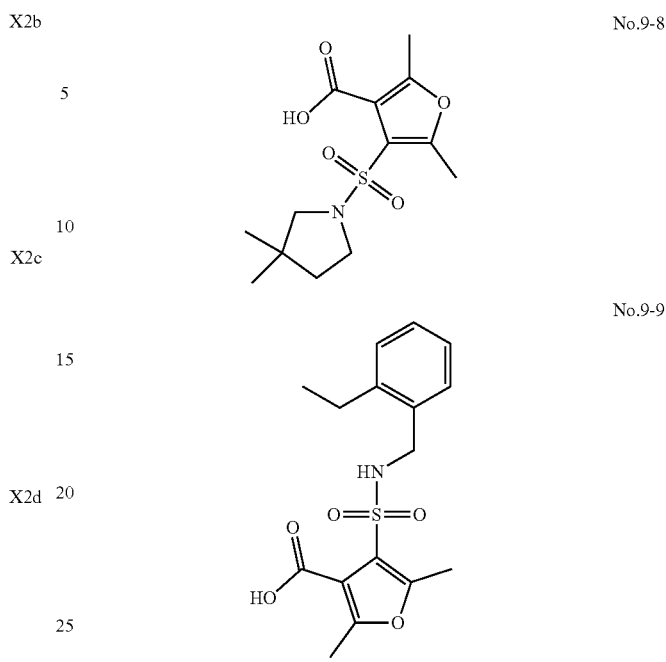

Among the compounds described above, for example, compound E, compound I, compound X2d, and the like are preferable.

1-6. Isomer

The compound represented by formula (1) encompasses stereoisomers and optical isomers, and these isomers are not particularly limited.

1-7. Salt, Hydrate, and Solvate

The salt of the compound represented by formula (1) is not particularly limited, as long as it is a pharmaceutically acceptable salt. The salt may be an acid salt or a basic salt. Examples of acid salts include inorganic acid salts, such as hydrochloride, hydrobromide, sulfate, nitrate, and phosphate; and organic acid salts, such as acetate, propionate, tartrate, fumarate, maleate, malate, citrate, methanesulfonate, and p-toluenesulfonate. Examples of basic salts include alkali metal salts, such as sodium salts and potassium salts; alkaline earth metal salts, such as calcium salts and magnesium salts; salts with ammonia; salts with organic amines, such as morpholine, piperidine, pyrrolidine, monoalkylamine, dialkylamine, trialkylamine, mono(hydroxyalkyl)amine, di(hydroxyalkyl)amine, and tri(hydroxyalkyl)amine; and the like.

The compound represented by formula (1) can also be a hydrate or a solvate. Examples of solvents include pharmaceutically acceptable organic solvents (e.g., ethanol, glycerol, and acetic acid), and the like.

2. Production Method

The compound represented by formula (1) can be synthesized by various methods. For example, a compound of formula (1) in which $R^6$ is a hydrocarbon group ($R^{6A}$), and $R^7$ and $R^8$ are both hydrogen atoms (compound 1d) can be synthesized, for example, according to the following reaction scheme or a scheme analogous to the following reaction scheme:

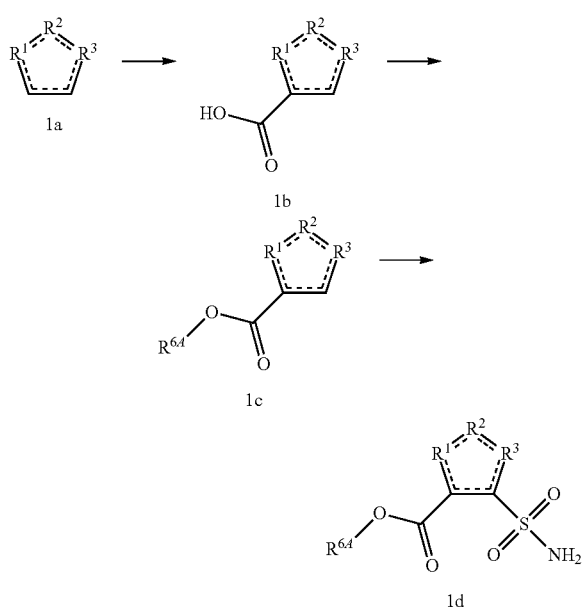

wherein $R^1$, $R^2$, $R^3$, $R^7$, and $R^8$ are the same as above; and $R^{6A}$ represents a hydrocarbon group.

Moreover, a compound of formula (1) in which $R^6$ is a hydrogen atom, and $R^7$ and $R^8$ are both hydrogen atoms (compound 1e) can be obtained, for example, by deprotecting the protecting group of the carboxyl group of compound 1d, i.e., $R^{6A}$—, using a strong base or the like.

Further, a compound in which at least one of $R^7$ and $R^8$ is a hydrocarbon group can be obtained by substituting the amino group of compound 1d or compound 1e with at least one hydrocarbon group.

Not only these methods, but also a Paal-Knorr reaction can be used to synthesize the compound represented by formula (1). Specifically, when a Paal-Knorr reaction is used, an appropriate ketoester/ketone coupling product (diketoester) can be reacted in the presence of, for example, an acid, ammonia, or a primary amine to synthesize furan or pyrrole (compound 1c); and the compound represented by formula (1) can then be synthesized according to the above reaction scheme.

When an amino group is present in $R^A$, $R^B$, etc., the compound represented by formula (1) can be synthesized, for example, by obtaining a compound in which the amino group on compound c is protected with an appropriate protecting group (e.g., phthalimide) as necessary (compound c') by a Paal-Knorr reaction; and performing deprotection at an appropriate time during the reaction process (for example, performing deprotection using hydrazine or the like).

2-1. Compound 1a→Compound 1b

In this step, compound 1b can be obtained by reacting compound 1a, an aluminum halide, and carbon dioxide.

The aluminum halide is not particularly limited. Examples include alkyl aluminum halides and the like. Preferable examples include dimethylaluminum chloride and the like.

The amount of aluminum halide is generally preferably 0.5 to 1.5 moles, and more preferably 0.8 to 1.2 moles, per mole of compound 1a, in terms of yield, ease of synthesis, and the like.

The amount of carbon dioxide is generally preferably 1 to 15 moles per mole of compound 1a, in terms of yield, ease of synthesis, and the like.

This step is preferably performed in a solvent. The solvent is not particularly limited. Examples of solvents include toluene and the like. The solvents may be used singly, or in a combination of two or more.

In this step, in addition to the above components, additives may be appropriately used as long as the effects of the present invention are not impaired.

The reaction atmosphere may generally be an inert gas atmosphere (e.g., an argon gas atmosphere or a nitrogen gas atmosphere). The reaction may be performed under heating, at room temperature, or under cooling; and is generally preferably performed at 0 to 100° C. (in particular, 15 to 40° C.). The reaction time is not particularly limited; and may generally be 3 to 48 hours, in particular 8 to 24 hours.

After completion of the reaction, a purification process can also be performed by a usual method, if necessary. Alternatively, the subsequent step can be performed without performing a purification process.

2-2. Compound 1b→Compound 1c

In this step, compound 1c can be obtained by reacting compound 1b, $R^{6A}$—OH, and a hydrogen halide.

The amount of $R^{6A}$—OH is generally preferably 3 to 15 parts by weight, and more preferably 5 to 10 parts by weight, per part by weight of compound 1b, in terms of yield, ease of synthesis, and the like.

The hydrogen halide is not particularly limited. Preferable examples include hydrogen chloride.

The amount of hydrogen halide is about 1 to 6 normal, and preferably about 1.5 to 5 normal, in the reaction liquid.

In this step, $R^{6A}$—OH generally functions as a solvent; however, suitable solvents may be further added. The solvents may be used singly, or in a combination of two or more.

In this step, in addition to the above components, additives may be appropriately used as long as the effects of the present invention are not impaired.

The reaction atmosphere may generally be an inert gas atmosphere (e.g., an argon gas atmosphere or a nitrogen gas atmosphere). The reaction may be performed under heating, at room temperature, or under cooling; and is generally preferably performed at 0 to 100° C. (in particular, 15 to 40° C.). The reaction time is not particularly limited; and may generally be 3 to 48 hours, in particular 8 to 24 hours.

After completion of the reaction, a purification process can also be performed by a usual method, if necessary. Alternatively, the subsequent step can be performed without performing a purification process.

2-3. Compound 1c→Compound 1d

In this step, compound 1d can be obtained by reacting compound 1c, a sulfonyl acid halide, and ammonium hydroxide. This step can also be performed in two stages; i.e., this step can be performed by reacting compound 1c with a sulfonyl acid halide, and then reacting the resulting reaction product with ammonium hydroxide.

The sulfonyl acid halide is not particularly limited. Preferable examples include sulfonyl acid chloride and the like.

The amount of sulfonyl acid halide is generally preferably 3 to 20 moles, and more preferably 7 to 15 moles, per mole of compound 1c, in terms of yield, ease of synthesis, and the like.

The amount of ammonium hydroxide is generally preferably 1 to 50 parts by weight, and more preferably 3 to 20 parts by weight, per part by weight of compound 1c, in terms of yield, ease of synthesis, and the like.

This step is preferably performed in a solvent. The solvent is not particularly limited. Examples of solvents include acetonitrile and the like. The solvents may be used singly, or in a combination of two or more.

In this step, in addition to the above components, additives may be appropriately used as long as the effects of the present invention are not impaired.

The reaction atmosphere may generally be an inert gas atmosphere (e.g., an argon gas atmosphere or a nitrogen gas atmosphere). The reaction may be performed under heating, at room temperature, or under cooling; and is generally preferably performed at 0 to 40° C. (in particular, 0 to 5° C.). The reaction time is not particularly limited; and may generally be 30 minutes to 10 hours, in particular 1 to 5 hours.

After completion of the reaction, a purification process can also be performed by a usual method, if necessary. Alternatively, the subsequent step can be performed without performing a purification process.

3. Use

The compound of the present invention has, for example, β-lactamase inhibitory activity, and activity of enhancing the antimicrobial effect of a β-lactam antimicrobial compound. Thus, the compound of the present invention can be used as an active ingredient of a medicament, a reagent, etc. (each of which may be referred to as "the pharmaceutical agent of the present invention" in the present specification). More specifically, the compound of the present invention can be used as an active ingredient of a β-lactamase inhibitor, an enhancer of the antimicrobial effect of a β-lactam antimicrobial compound, etc. Moreover, for example, an antimicrobial agent comprising the compound of the present invention and a β-lactam antimicrobial compound, and further an antimicrobial agent comprising a β-lactam antimicrobial compound, the agent being for use in administration in combination with the compound of the present invention (in the present specification, each of these may be referred to as "the pharmaceutical agent of the present invention"), can be provided by using the activities of the compound of the present invention, such as the β-lactamase inhibitory activity and the activity of enhancing the antimicrobial effect of a β-lactam antimicrobial compound.

Among the pharmaceutical agents of the present invention, pharmaceutical agents comprising the compound of the present invention are not particularly limited as long as they comprise the compound of the present invention, and may comprise other components as necessary. The other components are not particularly limited, as long as they are pharmaceutically acceptable. The other components include not only components with pharmacological action, but also additives. Examples of additives include bases, carriers, solvents, dispersants, emulsifiers, buffers, osmotic modulating agents, absorption promoters, stabilizers, excipients, binders, disintegrants, lubricants, thickeners, moisturizing agents, coloring agent, flavoring agents, chelating agents, and the like.

The β-lactamases to be inhibited by the compound of the present invention are not particularly limited as long as they are enzymes from any sources that catalyze β-lactam ring opening. β-lactamases (EC 3.5.2.6) are enzymes most commonly produced by bacteria. β-Lactamases catalyze the hydrolytic ring opening of β-lactam rings and are responsible for conferring bacterial resistance to β-lactam antimicrobial compounds, such as penicillins, penams, penems, cephems, cephalosporins, carbacephems, cephamycins, monobactams, and carbapenems. β-Lactamases are classified into classes A to D. Of these, class B β-lactamases are preferable, and class B1 β-lactamases are more preferable, as targets to be inhibited by the compound of the present invention. Specific examples include IMP-1, NDM-1, VIM-2, DIM-1, GIM-1, IDEM-1, SIM-1, SPM-1, TMB-1, BcII, BlaB, CcrA, IND-7, and the like. Examples of class B2 β-lactamases and class B3 β-lactamases respectively include SFH-1, GOB-1, and the like.

The β-lactam antimicrobial compound whose antimicrobial effect is to be enhanced by the compound of the present invention is not particularly limited. Examples include penicillin antimicrobial compounds, cephem antimicrobial compounds, carbapenem antimicrobial compounds, and the like.

Specific examples of penicillin antimicrobial compounds include benzylpenicillin, phenethicillin, cloxacillin, dicloxacillin, ampicillin, ciclacillin, amoxicillin, talampicillin, bacampicillin, lenampicillin, aspoxicillin, piperacillin, sulbenicillin, pivmecillinam, sultamicillin, phenoxymethylpenicillin, carbenicillin, azidocillin, propicillin, epicillin, ticarcillin, pirbenicillin, azlocillin, mezlocillin, and other known penicillin antimicrobial compounds.

Specific examples of cephem antimicrobial compounds include cefaclor, cefazolin, cefatrizine, cefadroxil, cephapirin, cefamandole nafate, cephradine, cephalexin, cephalothin, cefepime, cefoxitin, cefixime, cefodizime, cefditoren, cefdinir, cefsulodin, cefoselis, cefozopran, cefotaxime, ceftazidime, ceftaroline, cefotiam, ceftizoxime, ceftibuten, ceftezole, cefotetan, ceftriaxone, cefonicid, cefpiramide, cefpirome, cefbuperazone, cefprozil, cefoperazone, cefpodoxime, cefminox, cefmetazole, cefmenoxime, cefradine, cefroxadine, cefuroxime, latamoxef, flomoxef, ceftolozane (CXA101, (6R,7R)-3-[5-amino-4-[3-(2-aminoethyl)ureido]-1-methyl-1H-pyrazol-2-ium-2-ylmethyl]-7-[2-(5-amino-1,2,4-thiadiazol-3-yl)-2-[(Z)-1-carboxy-1-methylethoxyimino]acetamido]-3-cephem-4-carboxylic acid hydrogen sulfate salt), and other known cephem antimicrobial compounds.

Specific examples of carbapenem antimicrobial compounds include imipenem, panipenem, meropenem, biapenem, doripenem, ertapenem, tebipenem, and the like.

Examples of β-lactam antimicrobial compounds other than penicillin antimicrobial compounds, cephem antimicrobial compounds, and carbapenem antimicrobial compounds include aztreonam, carumonam, loracarbef, faropenem, ritipenem, and the like.

As the target bacteria of the pharmaceutical agent of the present invention, a wide range of gram-negative bacteria, gram-positive bacteria, and the like can be used. Examples of gram-negative bacteria include Enterobacteriaceae bacteria (e.g., bacteria of the genus *Escherichia*, bacteria of the genus *Klebsiella*, bacteria of the genus *Salmonella*, and bacteria of the genus *Shigella*), bacteria of the genus *Acinetobacter*, bacteria of the genus *Pseudomonas* (e.g., *Pseudomonas aeruginosa*), bacteria of the genus *Moraxella*, bacteria of the genus *Helicobacter*, bacteria of the genus *Campylobacter*, bacteria of the genus *Aeromonas*, bacteria of the genus *Vibrio* (e.g., *Vibrio cholerae* and *Vibrio parahaemolyticus*), bacteria of the genus *Haemophilus* (e.g., *Haemophilus influenzae*), bacteria of the genus *Neisseria* (e.g., *Neisseria gonorrhoeae* and *Neisseria meningitidis*), bacteria of the genus *Bacteroides*, and the like. Examples of gram-positive bacteria include bacteria of the genus *Staphylococcus* (e.g., *Staphylococcus aureus* and *Staphylococcus epidermidis*), enterococci (e.g., bacteria of the genus *Enterococcus*), bacteria of the genus *Streptococcus* (e.g., Group A streptococci, Group B streptococci, *Streptococcus pneumoniae*, and *Streptococcus viridans*), bacteria of the genus *Bacillus* (e.g., *Bacillus cereus* and *Bacillus anthracis*), bacteria of the genus *Clostridium* (e.g., *Clostridium tetani*, *Clostridium botulinum*, and *Clostridium difficile*), bacteria of the genus *Corynebacterium* (e.g., *Corynebacterium diphtheriae*), bacteria of the genus *Listeria*, bacteria of the genus *Lactobacillus*, bacteria of the genus *Bifidobacterium*, bacteria of the *Propionibacterium* (e.g., *Propionibacterium acnes*, which causes acne), actinomycete, and the like. Of these, gram-negative bacteria are preferable; and, for example, Enterobacteriaceae bacteria and bacteria of the genus *Acinetobacter* are more preferable. The pharmaceutical agent of the present invention can exert its effect on the target bacteria that produce β-lactamase.

The mode of using the pharmaceutical agent of the present invention is not particularly limited. An appropriate mode of use can be selected according to the type of pharmaceutical agent. The pharmaceutical agent of the present invention can be used, for example, in vitro (for example, added to a culture medium of cultured cells) or in vivo (for example, administered to an animal), according to the purpose of use.

The target for application of the pharmaceutical agent of the present invention when the agent is applied to an animal or cells is not particularly limited. Examples of target mammals include humans, monkeys, mice, rats, dogs, cats, rabbits, pigs, horses, bovine, sheep, goats, deer, and the like. Examples of cells include animal cells and the like. The kind of cell is also not particularly limited. Examples of cells include blood cells, hematopoietic stem cells/progenitor cells, gametes (spermatozoa, oocytes), fibroblasts, epithelial cells, vascular endothelial cells, nerve cells, hepatocytes, keratinocytes, muscle cells, epidermal cells, endocrine cells, ES cells, iPS cells, tissue stem cells, cancer cells, and the like.

The pharmaceutical agent of the present invention can be in any dosage form suitable for medicaments, reagents, and the like. Examples of dosage forms include oral dosage forms, such as tablets (e.g., orally disintegrating tablets, chewable tablets, effervescent tablets, lozenges, and jelly-like drops), pills, granules, fine granules, powders, hard capsules, soft capsules, dry syrups, liquids (including health drinks, suspensions, and syrups), and jelly formulations; and parenteral dosage forms, such as injectable formulations (e.g., drip infusions (e.g., formulations for intravenous drip infusion), intravenous injections, intramuscular injections, subcutaneous injections, and intradermal injections), topical agents (e.g., ointments, creams, plasters, and lotions), suppositories, inhalants, ophthalmic formulations, ophthalmic ointments, nasal drops, ear drops, and liposome formulations.

The administration route of the pharmaceutical agent of the present invention is not particularly limited, as long as the desired effect can be obtained. Examples include oral administration; parenteral administration including enteral administration, such as tube-feeding and enema administration, intravenous administration, intraarterial administration, intramuscular administration, intracardiac administration, subcutaneous administration, intradermal administration, and intraperitoneal administration; and the like.

The content of the active ingredient in the pharmaceutical agent of the present invention varies depending on, for example, the mode of use, the target of application, the condition of the target, etc.; and is not limited. For example, the content of the active ingredient may be 0.0001 to 100 wt %, and preferably 0.001 to 50 wt %.

The dosage of the pharmaceutical agent of the present invention in the case of administration to a human or an animal is not particularly limited, as long as it is a pharmaceutically effective amount. In the case of oral administration, in general, the dosage, in terms of the weight of the active ingredient, is 0.1 to 1000 mg/kg of body weight per day, and preferably 0.5 to 500 mg/kg of body weight per day. In the case of parenteral administration, the dosage is 0.01 to 100 mg/kg of body weight per day, and preferably 0.05 to 50 mg/kg of body weight per day. The above dosage can also be increased or decreased as appropriate depending on the age of a patient, disease state, symptoms, etc.

The β-lactamase inhibitor of the present invention can also be used for detection of β-lactamase-producing bacteria. For example, β-lactamase-producing bacteria can be detected by the presence or absence of growth inhibition when bacteria to be tested are cultured in the presence of a β-lactam antimicrobial compound and the β-lactamase inhibitor of the present invention. Specifically, this inhibitor can be used in, for example, the disk method and the broth microdilution method.

EXAMPLES

The present invention is described below in detail with reference to Examples. However, the present invention is not limited by the Examples.

1. Compound Preparation 1

Compounds A to I shown below were prepared.

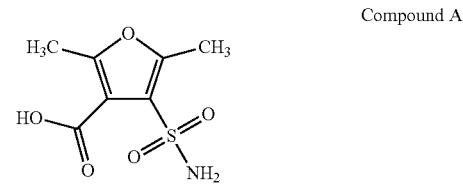

Compound A

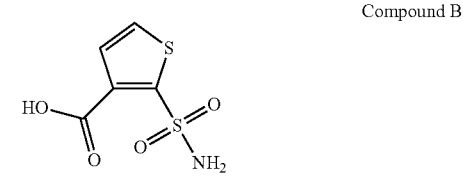

Compound B

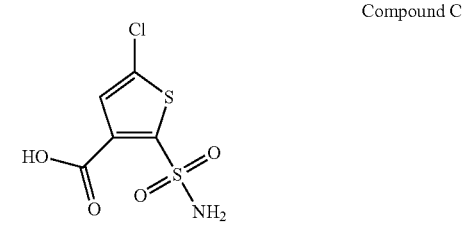

Compound C

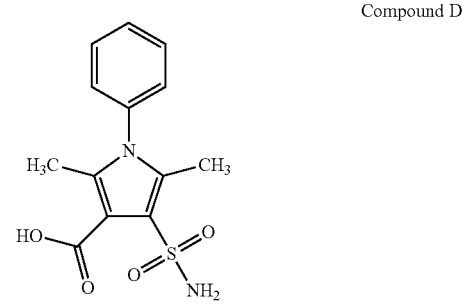

Compound D

Compound E

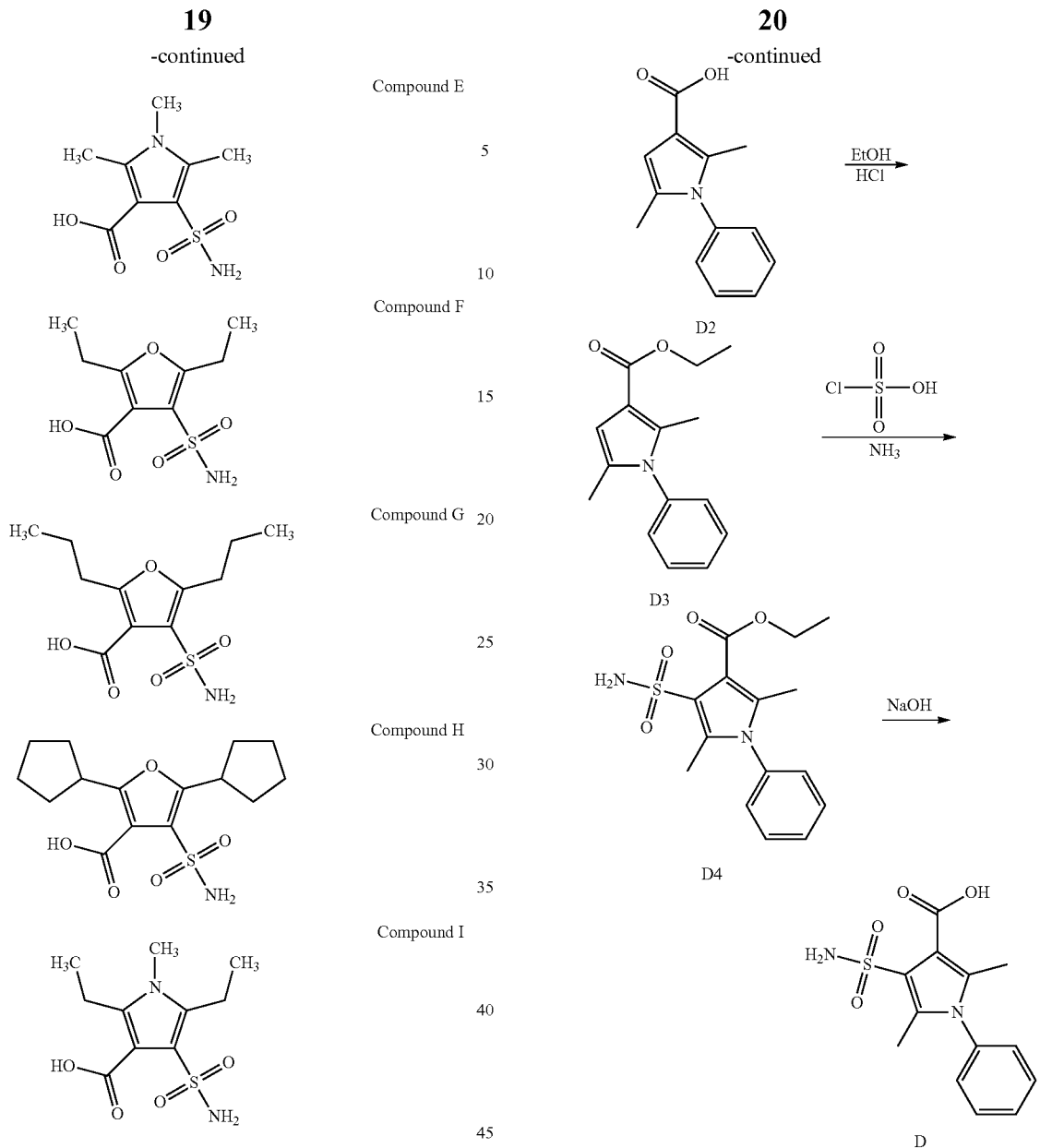

Compound F

Compound G

Compound H

Compound I

Compounds A to C were purchased from Enamine. Compounds D to I were synthesized according to the following Synthesis Examples 1 to 6.

Synthesis Example 1

Synthesis of Compound D

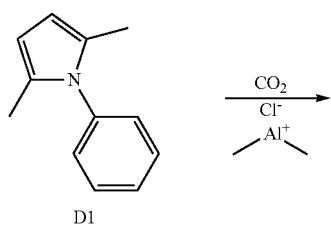

Compound D was synthesized according to the above reaction scheme. Specifically, compound D was synthesized as follows.

2,5-dimethyl-1-phenyl-1H-pyrrole (D1, 5.10 g, 29.8 mmol), dimethylaluminum chloride (2.74 g, 29.8 mmol), and CO$_2$ (10.0 g, 227 mmol) in dry toluene (200 mL) were stirred overnight. The mixture was quenched with water (200 mL), followed by extraction with dichloromethane (200 mL×3). The organic layer was dried over anhydrous Na$_2$SO$_4$, and concentrated under reduced pressure to obtain ethyl 2,5-dimethyl-1-phenylpyrrole-3-carboxylate (D2) as a yellow oil (2.73 g, 42.6%).

A solution of 2,5-dimethyl-1-phenylpyrrole-3-carboxylic acid (D2, 2.73 g, 12.7 mmol) in HCl/EtOH (20.0 mL, 4.00 N) was stirred overnight. The solution was concentrated under vacuum. The mixture was quenched with a 10.0% NaHCO$_3$ aqueous solution (100 mL), followed by extraction with dichloromethane (100 mL×3). The organic layer was dried over anhydrous Na$_2$SO$_4$, and concentrated under reduced pressure to obtain ethyl 2,5-dimethyl-1-phenylpyrrole-3-carboxylate (D3) as a yellow oil (1.70 g, 55.2%).

Sulfonyl acid chloride (8.10 g, 69.8 mmol) was slowly added at 0° C. to a solution of ethyl 2,5-dimethyl-1-phenylpyrrole-3-carboxylate (D3, 1.70 g, 6.99 mmol) in acetonitrile (30.0 mL). The solution was stirred for 2 hours, and ammonium hydroxide (10.0 mL) was then added. The solution was stirred for 1 hour, followed by extraction with ethyl acetate (100 mL×2). The organic layer was dried over anhydrous Na₂SO₄, and concentrated under reduced pressure to obtain a crude product. This crude product was purified by preparative HPLC to obtain ethyl 2,5-dimethyl-1-phenyl-4-sulfamoylpyrrole-3-carboxylate (D4) as a yellow oil (300 mg, 13.3%).

Ethyl 2,5-dimethyl-1-phenyl-4-sulfamoylpyrrole-3-carboxylate (D4, 300 mg, 0.932 mmol), NaOH (44.7 mg, 1.18 mmol), and water (3.00 mL) in MeOH (5.00 mL) were stirred for 16 hours. MeOH was removed under vacuum. The residue was added to ethyl acetate (10.0 mL) and water (10.0 mL). The pH of the mixture was adjusted to 3 to 4 with AcOH. The solution was extracted with ethyl acetate (10.0 mL×3). The organic layer was dried over anhydrous Na₂SO₄, and concentrated under reduced pressure to obtain compound D as a yellow solid (20.5 mg, 7.48%).

$^1$H-NMR (400 MHz, DMSO_d$_6$): δ 1.98-2.00 (m, 1H), 2.14 (s, 6H), 7.08 (s, 1H), 7.33-7.36 (m, 2H), 7.58-7.61 (m, 3H). MS Calcd.: 294; MS Found: 295.1 ([M+1]$^+$).

Synthesis Example 2

Synthesis of Compound E

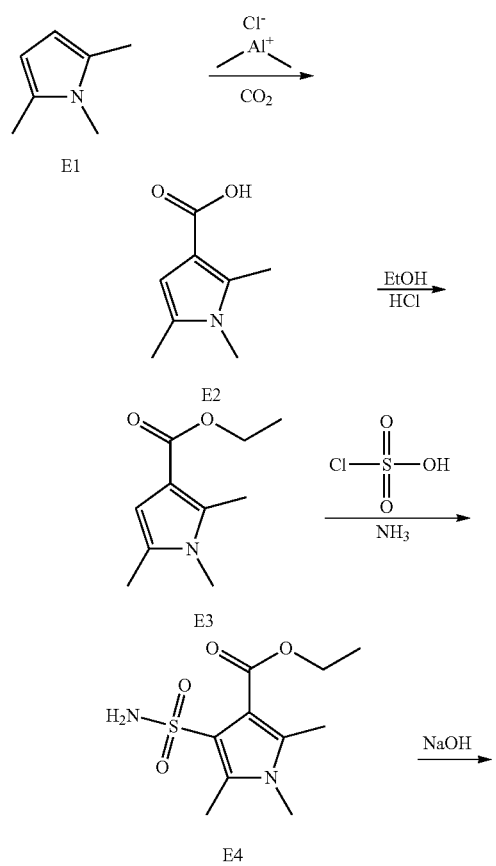

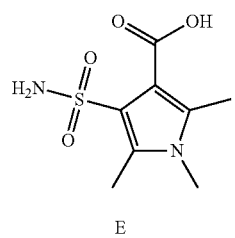

Compound E was synthesized in a manner similar to that of Synthesis Example 1, according to the above reaction scheme. Compound E was obtained as a yellow solid (yield: 20.0 mg (18.7%)).

$^1$H-NMR (400 MHz, CD$_3$OD): δ 2.35 (d, J=1.6 Hz, 2H), 2.48 (d, J=8.0 Hz, 6H), 3.46 (s, 3H). MS Calcd.: 232; MS Found: 233.1 ([M+1]$^+$).

Synthesis Example 3

Synthesis of Compound F

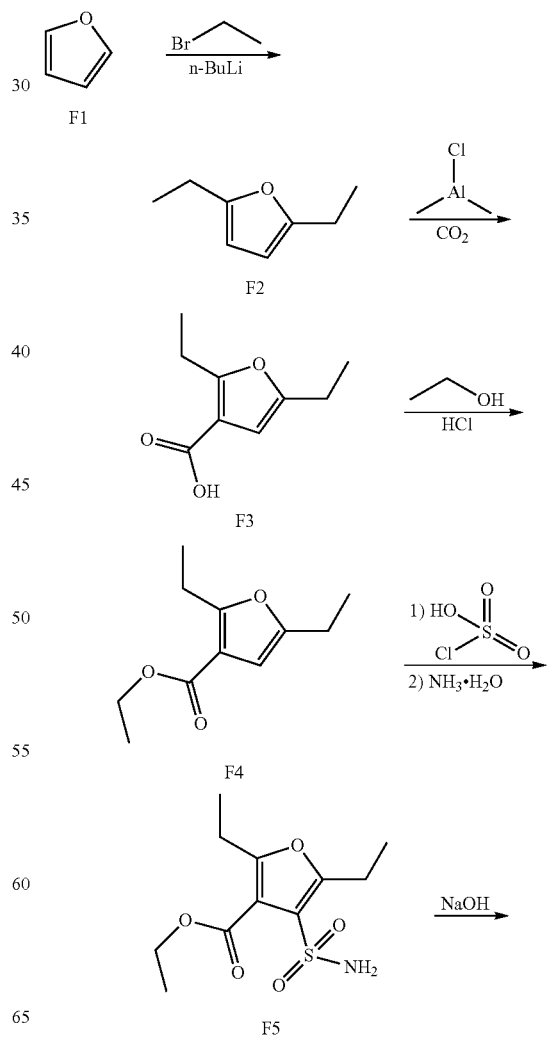

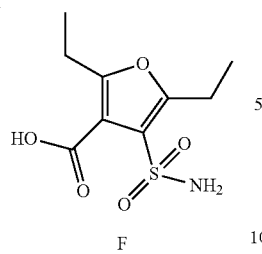

F

Compound F was synthesized according to the above reaction scheme. Specifically, compound F was synthesized as follows.

A solution of furan (F1, 16.0 g, 0.235 mol) and TMEDA (60.0 g, 0.517 mol) was cooled at 0° C., and N-butyllithium (in hexane, 2.50 M, 207 mL, 0.517 mol) was added dropwise. The temperature of the solution was returned to room temperature, and the solution was stirred for 1 hour. Bromoethane (76.8 g, 0.705 mol) in tetrahydrofuran (150 mL) was added dropwise. The mixture was stirred at room temperature overnight and quenched with saturated ammonium chloride (300 mL), followed by extraction with methyl tert-butyl ether (500 mL×2). The organic layer was washed with 1N HCl aqueous solution (100 mL×3), dried over anhydrous $Na_2SO_4$, and concentrated under reduced pressure to obtain 2,5-diethylfuran (F2) as a yellow oil (18.9 g, 64.9%).

A solution of 2,5-diethylfuran (F2, 17.0 g, 0.137 mol), dimethylaluminum chloride (152 mL, 0.9 M, 0.137 mol), and $CO_2$ (20.0 g, 0.454 mol) in dry toluene (200 mL) was stirred overnight. The mixture was quenched with water (250 mL), followed by extraction with dichloromethane (300 mL×3). The organic layer was dried over anhydrous $Na_2SO_4$, and concentrated under reduced pressure to obtain 2,5-diethylfuran-3-carboxylic acid (F3) as a reddish-brown solid (3.6 g, 15.7%).

A solution of 2,5-diethylfuran-3-carboxylic acid (F3, 3.6 g, 0.021 mol) in HCl/EtOH (36.0 mL, 2.00 N) was stirred overnight. The solution was concentrated under vacuum. The mixture was quenched with a 10.0% $NaHCO_3$ aqueous solution (100 mL), followed by extraction with dichloromethane (100 mL×2). The organic layer was dried over anhydrous $Na_2SO_4$ and concentrated under reduced pressure to obtain ethyl 2,5-diethylfuran-3-carboxylate (F4) (2.67 g, 63.6%).

Chlorosulfuric acid (15.0 g, 0.130 mol) was slowly added at 0° C. to a solution of ethyl 2,5-diethylfuran-3-carboxylate (F4, 2.50 g, 0.013 mol) in acetonitrile (30.0 mL). The solution was stirred for 2 hours, and ammonium hydroxide (50.0 mL) was then added. The solution was stirred for 1 hour. The solution was extracted with ethyl acetate (100 mL×2). The organic layer was dried over anhydrous $Na_2SO_4$, and concentrated under reduced pressure to obtain a crude product. The crude product was purified using a column to obtain ethyl 2,5-diethyl-4-sulfamoylfuran-3-carboxylate (F5) as a yellow solid (880 mg, 25.1%).

A solution of ethyl 2,5-diethyl-4-sulfamoylfuran-3-carboxylate (F5, 880 mg, 3.20 mmol), NaOH (640 mg, 16.0 mmol), and water (4.00 mL) in MeOH (10.0 mL) was stirred for 16 hours. MeOH was removed under vacuum. Ethyl acetate (50.0 mL) and water (20.0 mL) were added to the residue. The pH of the mixture was adjusted to 3 to 4 with aqueous HCl (1N). The solution was extracted with ethyl acetate (40.0 mL×3). The organic layer was dried over anhydrous $Na_2SO_4$, and concentrated under reduced pressure to obtain compound F as a yellow solid (120 mg, 15.2%). $^1$H-NMR (400 MHz, $CDCl_3$): δ 5.66 (s, 2H), 3.00-3.04 (m, 4H), 1.24-1.30 (m, 6H). MS Calcd.: 247; MS Found: 248.1 ([M+1]$^+$).

Synthesis Example 4

Synthesis of Compound G

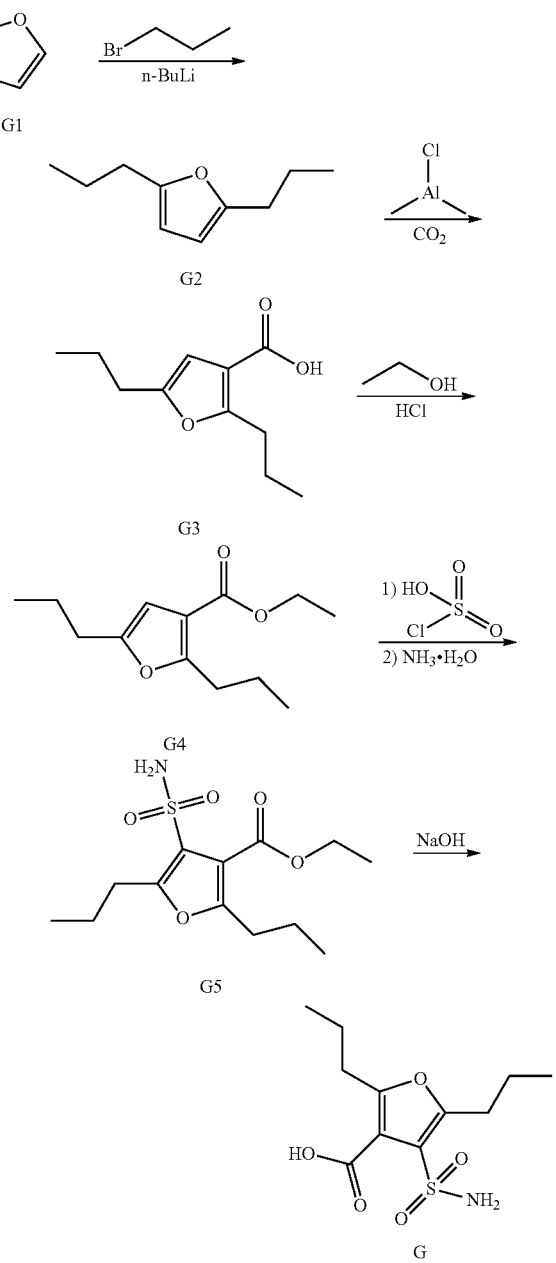

Compound G was synthesized in a manner similar to that of Synthesis Example 3, according to the above reaction scheme. Compound G was obtained as a yellow solid (yield: 0.130 g (13.0%)).

$^1$H-NMR (400 MHz, $CD_3OD$): δ 2.92-2.99 (m, 4H), 1.66-1.76 (m, 4H), 0.94-0.99 (m, 6H). MS Calcd.: 275; MS Found: 276.0 ([M+1]$^+$).

Synthesis Example 5

Synthesis of Compound H

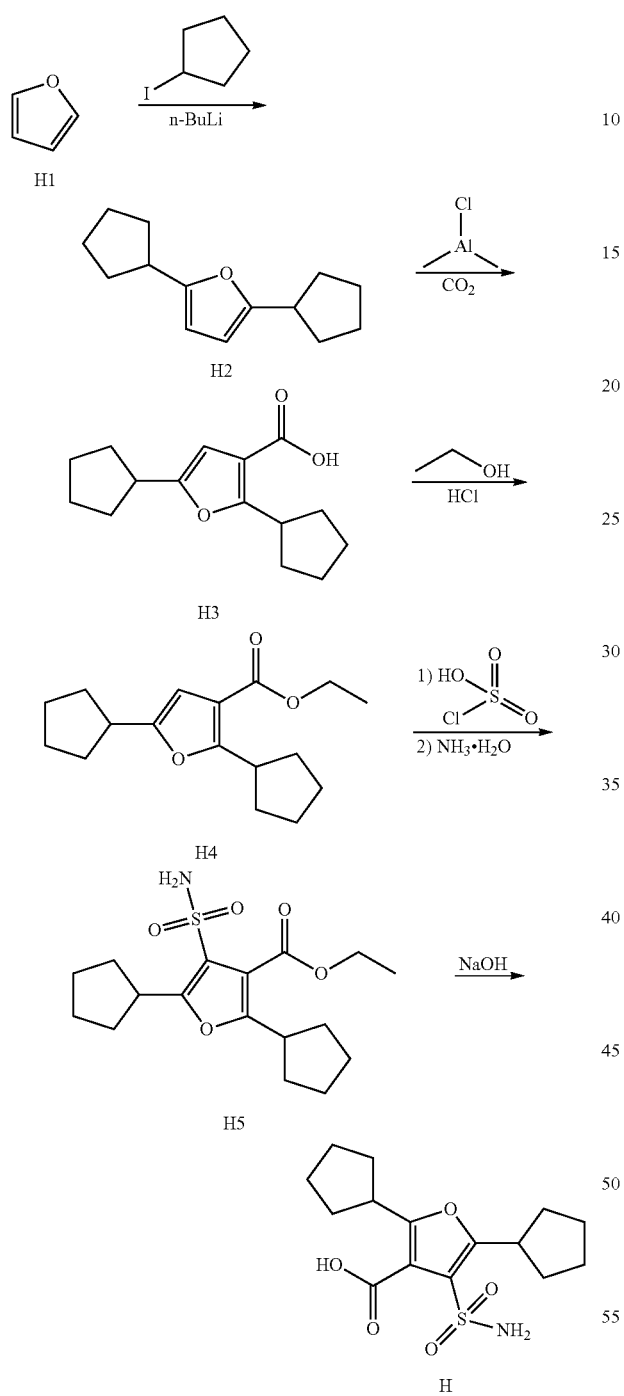

H

Compound H was synthesized in a manner similar to that of Synthesis Example 3, according to the above reaction scheme. Compound H was obtained as a yellow solid (yield: 0.135 mg (18.3%)).

$^1$H-NMR (400 MHz, CDCl$_3$): δ 1.45-2.12 (m, 16H), 3.83-3.95 (m, 2H). MS Calcd: 327; MS Found: 326.0 ([M−1]$^−$).

Synthesis Example 6

Synthesis of Compound I

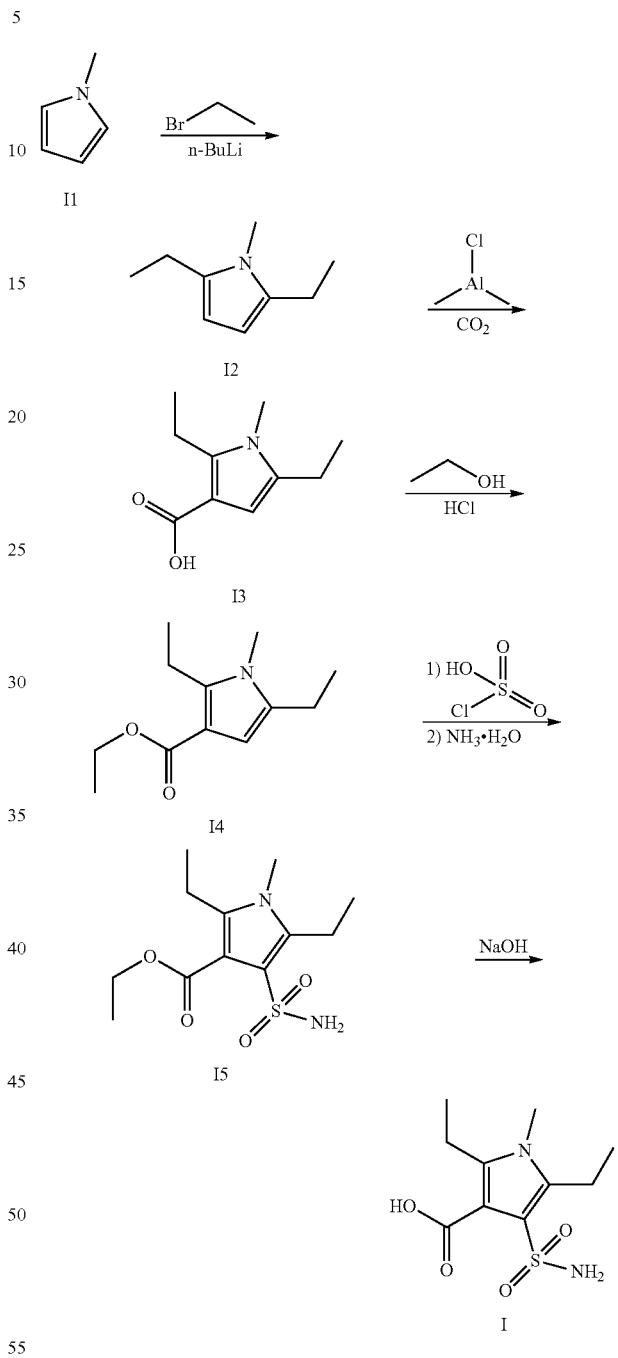

I

Compound I was synthesized in a manner similar to that of Synthesis Example 1, according to the above reaction scheme. Compound I was obtained as a yellow solid (yield: 110 mg (11.1%)). $^1$H-NMR (400 MHz, CD$_3$OD): δ 3.45 (s, 3H), 2.88-2.94 (m, 4H), 1.04-1.11 (m, 6H). MS Calcd.: 260; MS Found: 261.1 ([M+1]$^+$).

2. Compound Analysis 1

The compounds were analyzed for their activity, complexed structure, toxicity, and the like (Test Examples 1 to 7).

Test Example 1

Drug Susceptibility Test 1

Plates for drug susceptibility test measurement were prepared by using 96- or 384-well U-bottom plates, a Mueller-Hinton liquid medium, and antimicrobial drugs (ceftazidime (CAZ), imipenem (IPM), meropenem (MPM), doripenem (DPM), and biapenem (BPM)). A 1/2 antimicrobial drug dilution series was made up to well 11 of, for example, a 96-well U-bottom plate so that the leftmost well 1 of row A contained an antimicrobial drug at the maximum concentration, the antimicrobial drug concentration in well 2 to the right of well 1 was 1/2 of the maximum concentration, the antimicrobial drug concentration in well 3 to the right of well 2 was 1/4 of the maximum concentration, and so on. Well 12 was a blank well that did not contain the antimicrobial drug. An antimicrobial drug dilution series was made in each of rows B and C in the same manner as in row A. Further, 10 μg/mL and 50 μg/mL of a test substance (compound A) were added to row B and row C, respectively (FIG. 1).

Bacteria into which a plasmid encoding a class B β-lactamase (metallo-β-lactamase (MBL): NDM-1, or VIM-2) was introduced (pBCSK (+)/*E. coli* DH5a) were used as test bacteria. The test bacteria were adjusted to $10^8$ cfu/mL with a Mueller-Hinton medium. Further, the test bacteria were diluted 10-fold with a Mueller-Hinton medium ($10^7$ cfu/mL). 5 μl of the test bacteria was collected and inoculated into the plates for drug susceptibility test measurement. After overnight culture at 35° C., the growth of the test bacteria was visually checked. The concentration of the antimicrobial drug in a well containing the lowest concentration of the antimicrobial drug among the wells in which no growth of the test bacteria was confirmed was defined as the minimal inhibitory concentration value (FIG. 1).

Table 1 shows the results. In Table 1, the "MBLs" column indicates class B β-lactamases produced by the test bacteria, and the empty vector indicates that no class B lactamase is produced.

TABLE 1

| | | MIC (μg/mL) | | | | | |
|---|---|---|---|---|---|---|---|
| MBLs | Subclass | CAZ | CAZ + compound A (10 μg/ml) | CAZ + compound A (50 μg/ml) | MPM | MPM + compound A (10 μg/ml) | MPM + compound A (50 μg/ml) |
| IMP-1 | B1 | 256 | 2 | 1 | 0.5 | 0.031 | 0.031 |
| NDM-1 | B1 | >1,024 | 256 | 64 | 16 | 0.25 | 0.063 |
| VIM-2 | B1 | 4 | 1 | 0.5 | 0.063 | 0.031 | 0.031 |
| Empty vector | — | 0.25 | 0.25 | 0.25 | 0.016 | 0.016 | 0.016 |

As shown in Table 1, the addition of compound A decreases the MICs of the antimicrobial drugs against the β-lactamase-producing bacteria.

Test Example 2

β-Lactamase Inhibitory Activity Measurement Test

Each individual class B β-lactamase (IMP-1, NDM-1, or VIM-2; final concentration: 10 nM), imipenem (final concentration: 100 μM), and each individual test substance (compound A or compound Z shown below; final concentrations: 0, 1, 10, 100 μM) were mixed in an HEPES buffer. The imipenem decomposition activity (Dabs/min) under the conditions of absorbance: 298 nm and temperature: 30° C. was measured. The imipenem decomposition activity when no test substance was added was defined as 100%, and the imipenem residual decomposition activity when each test substance was individually added was plotted.

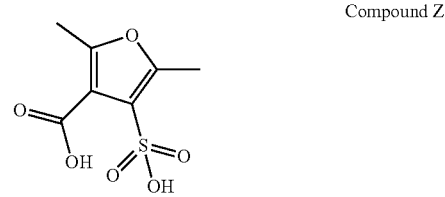

Compound Z

Figure 2:
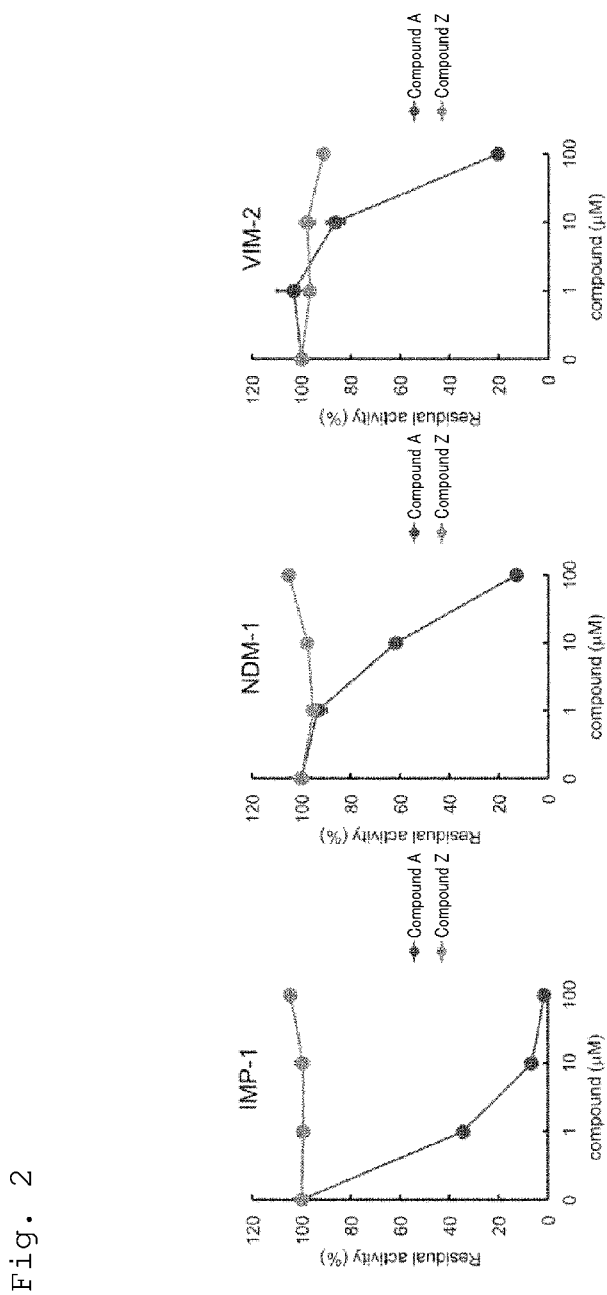
FIG. 2 shows the results of the β-lactamase inhibitory activity measurement test of Test Example 2. The vertical axis shows the imipenem residual decomposition activity, and the horizontal axis shows the concentrations of test substances. Above each graph, the class B β-lactamase used is shown.

FIG. 2 shows the results. As shown in FIG. 2, compound A was found to inhibit β-lactamases.

Test Example 3

Drug Susceptibility Test 2

The test was performed in the same manner as in Test Example 1, except that various strains of Enterobacteriaceae bacteria that produce class B β-lactamases were used as test bacteria.

Figure 3:
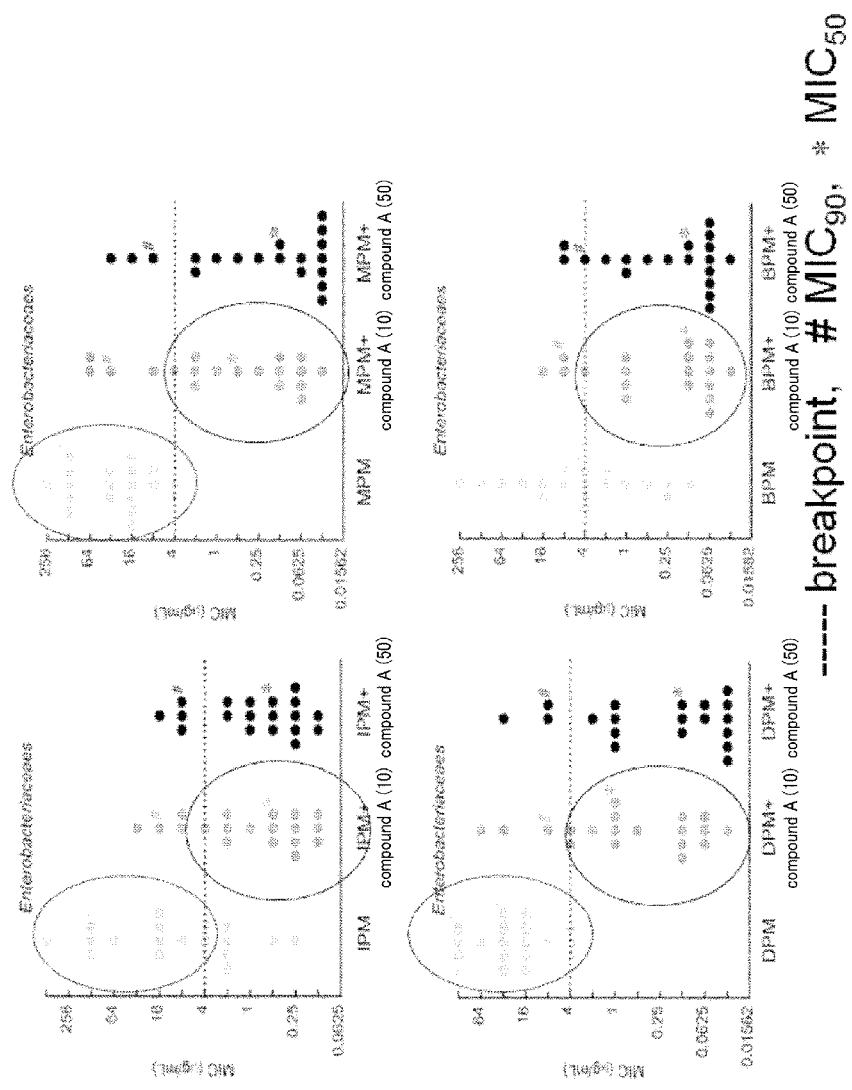
FIG. 3 shows the results of the drug susceptibility test of Test Example 3. The vertical axis shows the MIC; and the horizontal axis shows the antimicrobial drug used, and the kind of test substance (compound A) and the concentration (µg/mL) thereof. The plots each show data on respective test strains.

FIG. 3 shows the results. As shown in FIG. 3, the addition of compound A decreases the MICs of the antimicrobial drugs against the β-lactamase-producing Enterobacteriaceae bacteria.

Test Example 4

Drug Susceptibility Test 3

The test was performed in the same manner as in Test Example 1, except that various strains of *Acinetobacter* that produce class B β-lactamases were used as test bacteria.

Figure 4:
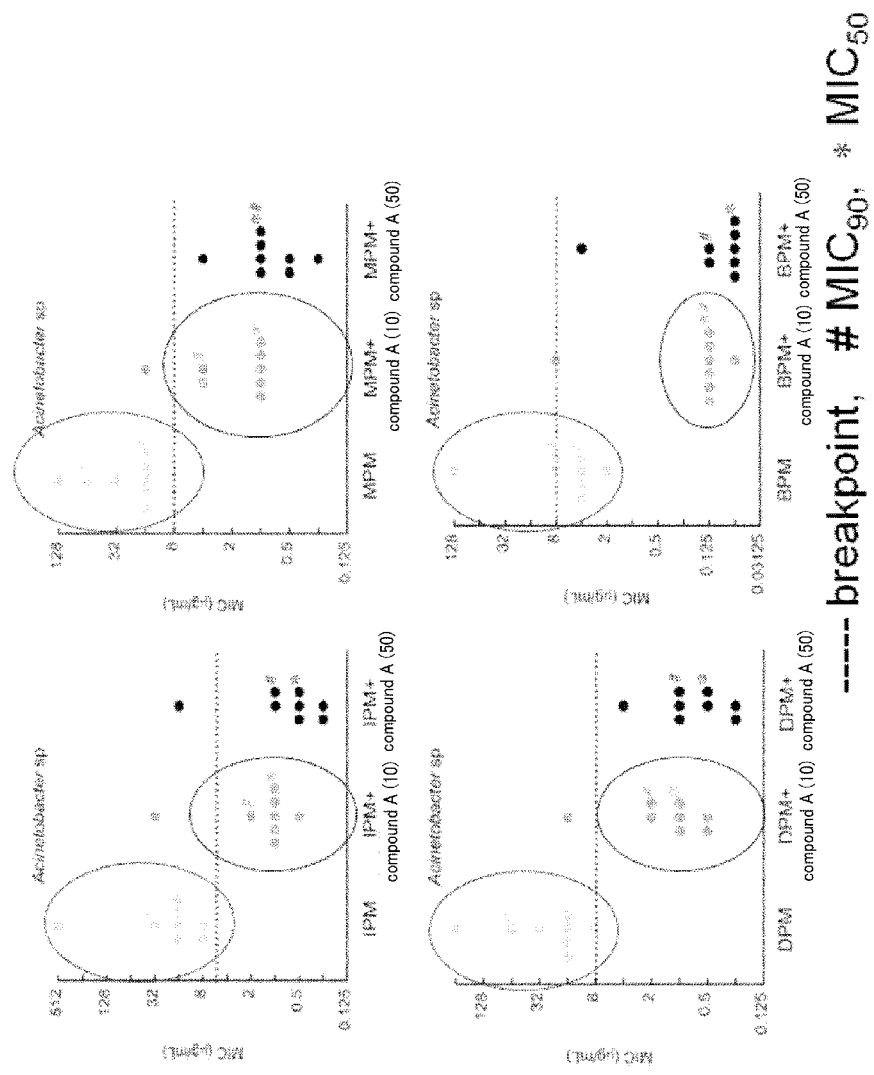
FIG. 4 shows the results of the drug susceptibility test of Test Example 4. The vertical axis shows the MIC; and the horizontal axis shows the antimicrobial drug used, and the kind of test substance (compound A) and the concentration (µg/mL) thereof. The plots each show data on respective test strains.
Figure 5:
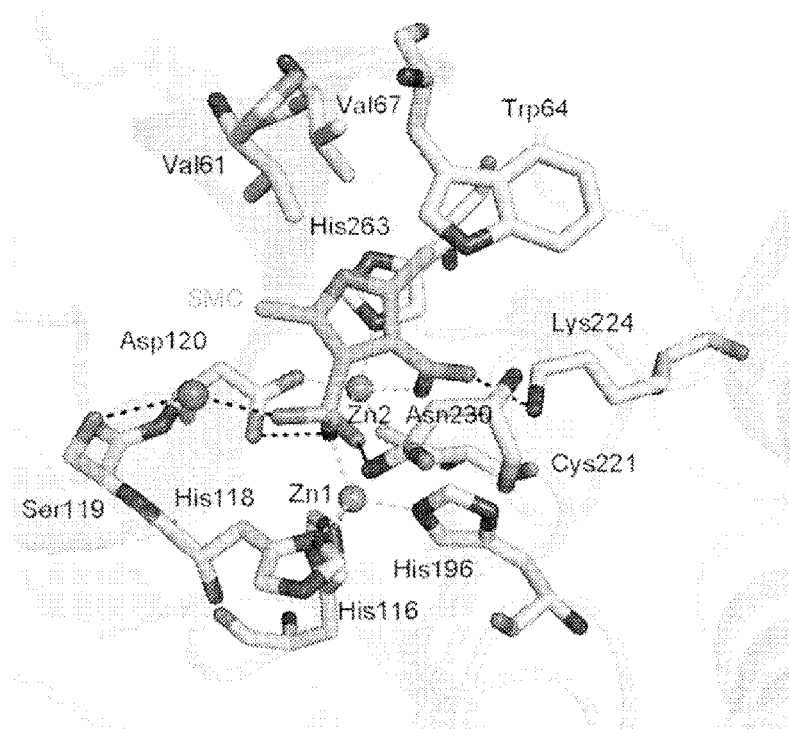
FIG. 5 is a schematic diagram of the IMP-1-compound A complexed structure obtained by X-ray crystallography in Test Example 5.
Figure 6:
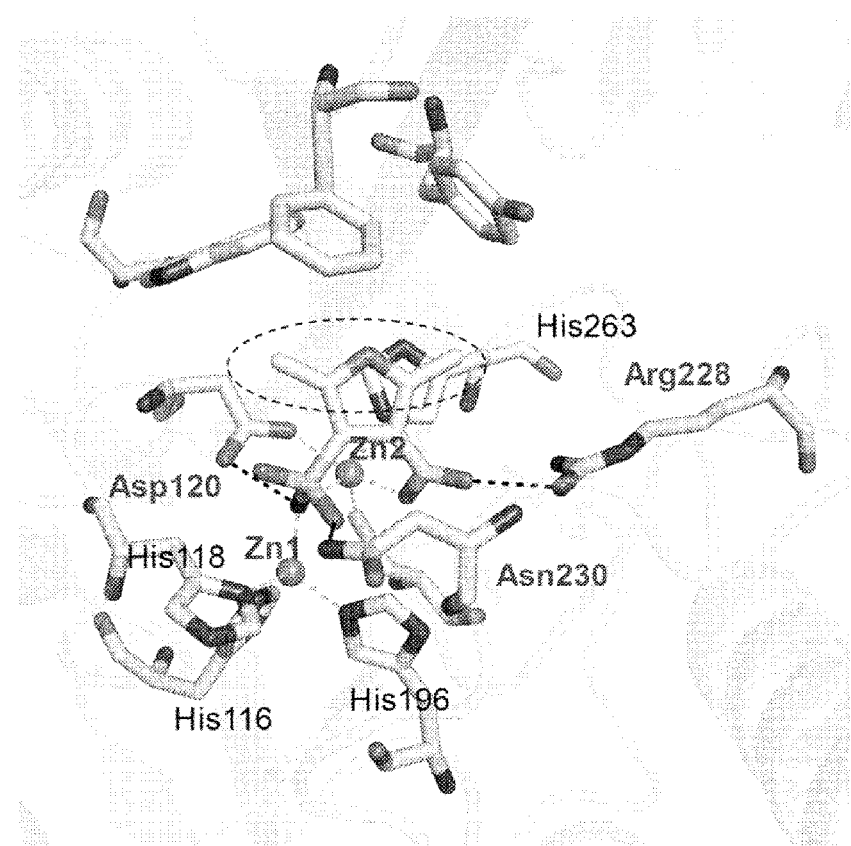
FIG. 6 is a schematic diagram of the VIM-2-compound A complexed structure obtained by X-ray crystallography in Test Example 5.
Figure 7:
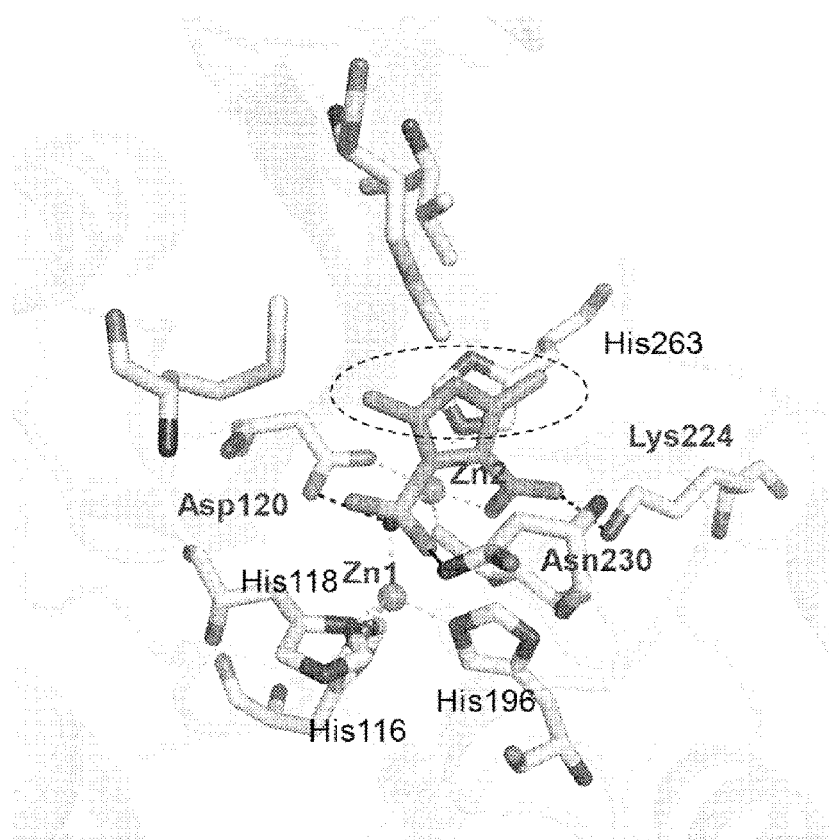
FIG. 7 is a schematic diagram of the NDM-1-compound A complexed structure obtained by X-ray crystallography in Test Example 5.
Figure 8:
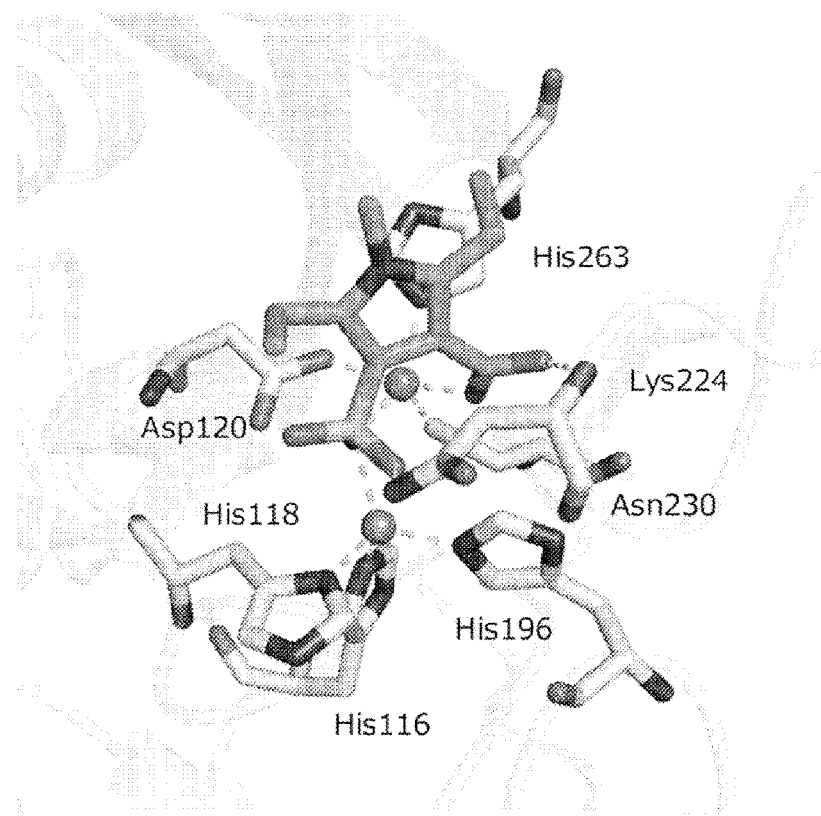
FIG. 8 is a schematic diagram of the NDM-1-compound I complexed structure obtained by X-ray crystallography in Test Example 5.

FIG. 4 shows the results. As shown in FIG. 4, the addition of compound A decreases the MICs of the antimicrobial drugs against the β-lactamase-producing *Acinetobacter*.

Test Example 5

X-Ray Crystallography

Analysis of Complexed Structure of IMP-1 and Test Substance

*Escherichia coli* that produces IMP-1 (pET9a-ΔIMP-1/*E. coli* BL21 (DE3)) was liquid-cultured, and the cells were collected by centrifugation. After the cells were sonicated, the cells were separated into a soluble fraction and an insoluble fraction by ultracentrifugation. The soluble fraction was passed through a cation exchange column, a hydrophobic interaction column, and a gel filtration column in this order to purify IMP-1. The purified IMP-1 was concentrated after replacement with an HEPES buffer, using an ultrafiltration column. The purified IMP-1 (15 mg/mL) and a reservoir solution (100 mM HEPES (pH 7.5), 200 mM sodium acetate, 25% PEG3350) were mixed, followed by incubation at 20° C., thereby obtaining IMP-1 crystals. The IMP-1 crystals were infiltrated with a reservoir solution described above in which a test substance (compound A) was dissolved to prepare crystals of a complex of IMP-1 and the test substance. The complex crystals were irradiated with X-ray synchrotron radiation using a synchrotron to collect diffraction data. The phase was determined by molecular replacement, using publicly available information about the structure of IMP-1. Refmac5 was used for refinement, and coot was used for model building.

Analysis of Complexed Structure of VIM-2 and Test Substance

*Escherichia coli* that produces VIM-2 (pET29a-VIM-2/*E. coli* BL21 (DE3)) was liquid-cultured, and the cells were collected by centrifugation. After the cells were sonicated, the cells were separated into a soluble fraction and an insoluble fraction by ultracentrifugation. The soluble fraction was passed through an anion exchange column, a hydrophobic interaction column, and a gel filtration column in this order to purify VIM-2. The purified VIM-2 was concentrated after replacement with a Tris-HCl buffer, using an ultrafiltration column. The purified VIM-2 (15 mg/mL) and a reservoir solution (200 mM magnesium formate, 25% PEG3350) were mixed, followed by incubation at 20° C., thereby obtaining VIM-2 crystals. The VIM-2 crystals were infiltrated with a reservoir solution described above in which a test substance (compound A) was dissolved to prepare crystals of a complex of VIM-2 and the test substance. X-ray diffraction data regarding the complex crystals were collected using a synchrotron. The phase was determined by molecular replacement, using publicly available information about the structure of VIM-2. Refmac5 was used for refinement, and coot was used for model building.

Analysis of Complexed Structure of NDM-1 and Test Substance

*Escherichia coli* that produces NDM-1 (pET28a-NDM-1/*E. coli* BL21 (DE3)) was liquid-cultured, and the cells were collected by centrifugation. After the cells were sonicated, the cells were separated into a soluble fraction and an insoluble fraction by ultracentrifugation. The soluble fraction was passed through a nickel column, an anion exchange column, and a gel filtration column in this order to purify NDM-1. The purified NDM-1 was concentrated after replacement with a Tris-HCl buffer, using an ultrafiltration column. The purified NDM-1 (40 mg/mL) and a reservoir solution (100 mM Bis-Tris (pH 6.1), 200 mM ammonium sulfate, 25% PEG3350) were mixed, followed by incubation at 20° C., thereby obtaining NDM-1 crystals. The NDM-1 crystals were infiltrated with a reservoir solution described above in which a test substance (compound A or compound I) was dissolved to prepare crystals of a complex of NDM-1 and the test substance. X-ray diffraction data regarding the complex crystals were collected using a synchrotron. The phase was determined by molecular replacement, using publicly available information about the structure of NDM-1. Refmac5 was used for refinement, and coot was used for model building.

Results

FIGS. 5 to 8 show the results. As shown in FIGS. 5 to 8, the test substances were found to interact with IPM-1, VIM-2, and NDM-1 via their sulfamoyl and carboxy groups. There is a certain space between the side ($R^1$, $R^2$, and $R^3$ side in formula (1)) opposite to the side to which these groups are linked, and IPM-1, VIM-2, and NDM-1; thus, this opposite side was considered to have a high degree of freedom in its structure.

Test Example 6

Drug Susceptibility Test 4 and Inhibition Constant (Ki) Measurement Test 1

The drug susceptibility test was performed in the same manner as in Test Example 1, except that compounds A to C and E to I were used as test substances.

The inhibition constant (Ki) measurement test was performed in the following manner. The inhibition constant (Ki) was measured using various metallo-β-lactamases (final concentration: 10 nM). The imipenem decomposition activity (Δabs/min) at each point under the conditions of absorbance: 298 nm and temperature: 30° C. was measured by varying the concentration of imipenem as a substrate and the concentrations of test substances (compounds A to E) as inhibitors. Each measured value was fitted to the Lineweaver-Burk plot equation to calculate Ki.

Table 2 shows the results. In Table 2, the leftmost column indicates the test substances, and the term "None" indicates the case in which no test substance was added.

TABLE 2

| | Inhibition constant $K_i$ (μM) | | | IMP-1 meropenem | NDM-1 meropenem +2 mg $l^{-1}$ compound | VIM-2 ceftazidime |
|---|---|---|---|---|---|---|
| compounds | IMP-1 | NDM-1 | VIM-2 | | | |
| None | | | | 1 | 64 | 16 |
| B | 34.1 | 7.68 | 15.5 | 0.5 | 16 | 16 |
| C | 19.1 | 19.3 | 2.29 | 0.5 | 64 | 16 |
| A | 0.22 | 9.82 | 2.80 | 0.06 | 16 | 16 |
| F | 0.30 | 0.92 | 1.01 | 0.03 | 0.25 | 16 |
| G | 0.38 | 0.29 | 0.46 | 0.13 | 1 | 32 |
| H | 1.27 | 0.18 | 0.76 | 0.5 | 2 | 32 |
| E | 1.23 | 9.08 | 0.42 | 0.13 | 4 | 4 |
| I | 2.14 | 0.84 | 0.02 | 0.03 | 0.25 | 1 |
| D | 7.51 | 10.2 | 20.8 | 1 | 16 | 32 |

As shown in Table 2, the addition of compounds A to C and E to I each individually decreases the MICs of the antimicrobial drugs against the β-lactamase-producing bacteria, and inhibits β-lactamase activity.

Test Example 7

Toxicity Evaluation Test

Various concentrations of a test substance (compound A) or staurosporine were added to HeLa cells, and live cells were counted using an MTT assay kit (Promega Cat No. G4000).

Figure 9:
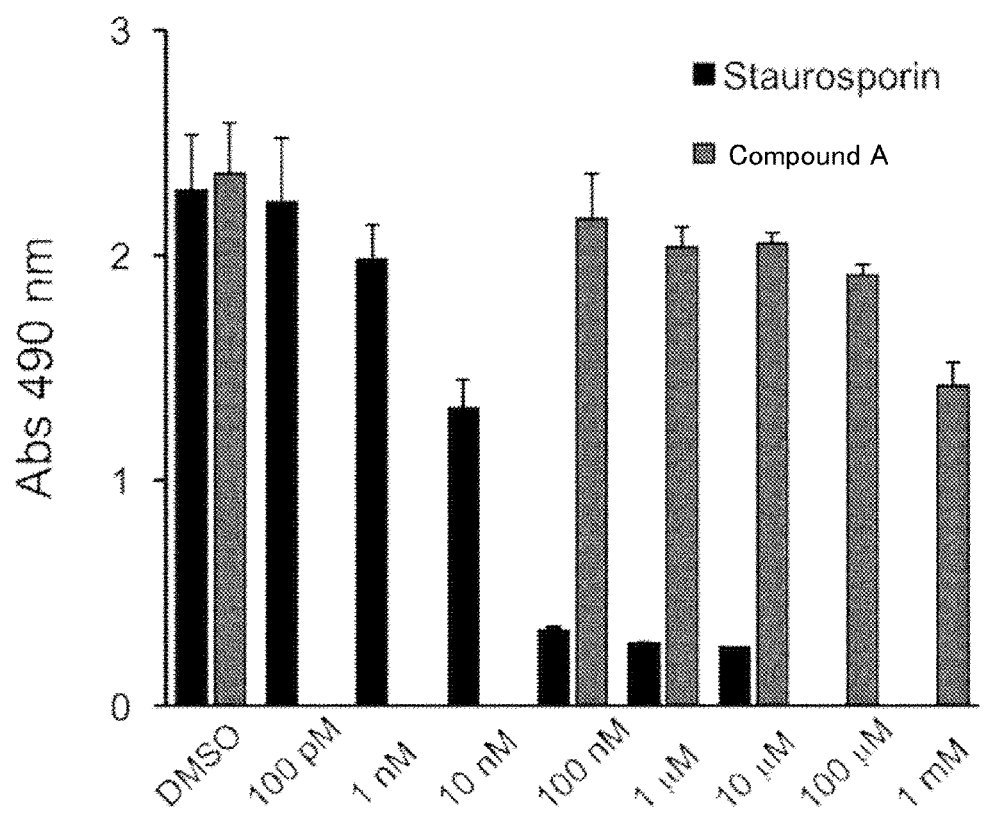
FIG. 9 shows the results of the toxicity evaluation test of Test Example 7. The vertical axis shows the absorbance reflecting live cells, and the horizontal axis shows the concentration of a test substance. In the horizontal axis, DMSO indicates the case in which no test substance was added.

FIG. 9 shows the results. As shown in FIG. 9, the toxicity of compound A was found to be very low.

Test Example 8

Reverse Mutation Test (Ames Test)

Compound A was used as a test substance. The Ames test was entrusted to UBE Scientific Analysis Laboratory, Inc. As a result, compound A was found to be negative in the Ames test.

3. Compound Preparation 2

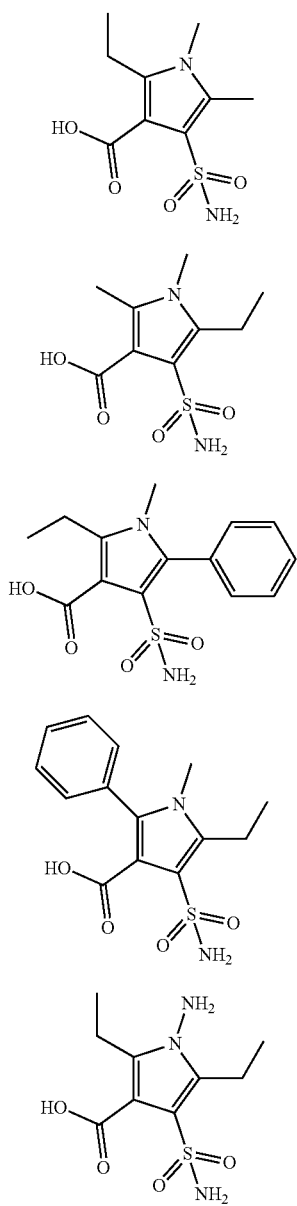

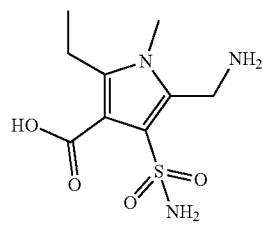

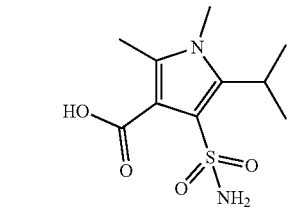

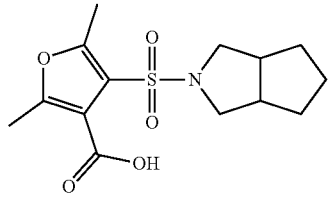

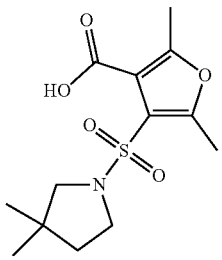

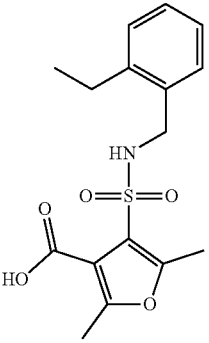

Compounds X2a, X2b, X2c, X2d, X3a, and X4 were synthesized according the following Synthesis Examples 7 to 8. Compound X3b can be synthesized according the following Synthesis Example 9. Compounds No. 9-7, No. 9-8, and No. 9-9 were purchased from Namiki Shoji Co., Ltd.

Synthesis Example 7

Synthesis of Compounds X2a, X2b, X2c, X2d, and X4

Desired product 8 (compounds X2a, X2b, X2c, X2d, and X4) was synthesized by the following synthetic route.

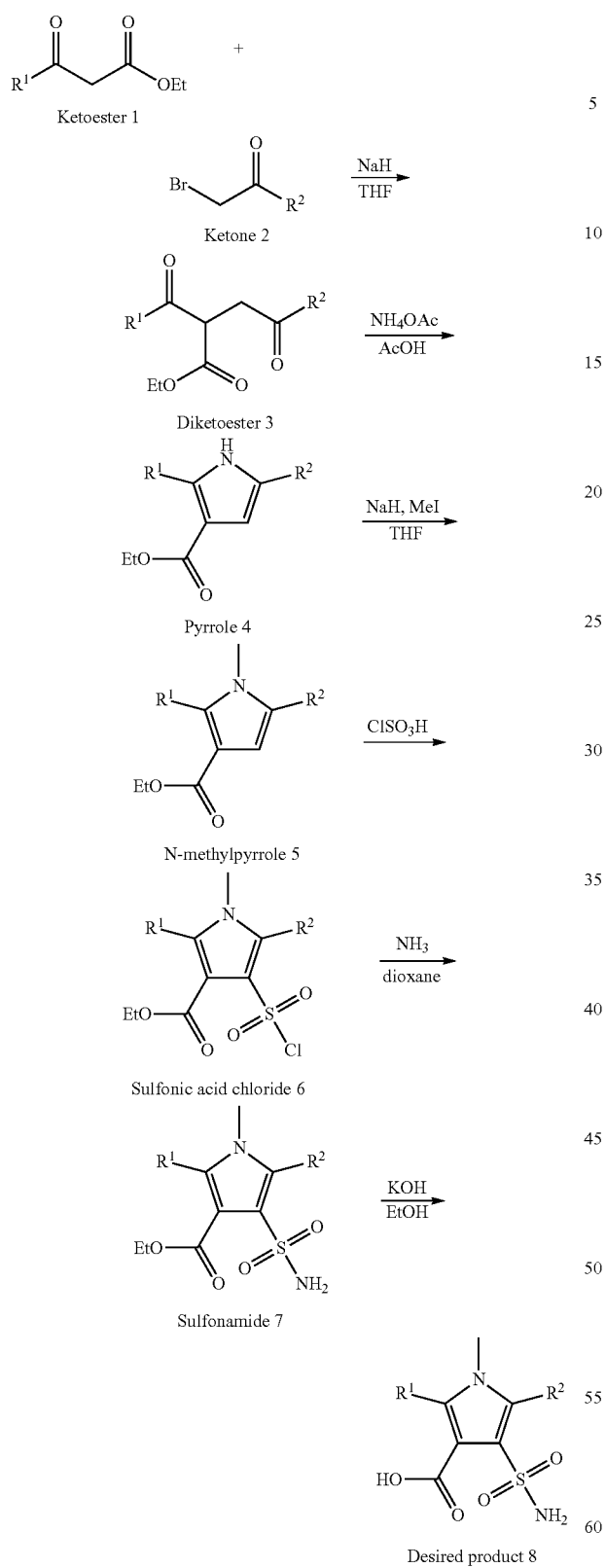

alphabetical letters shown after the number indicate that they are compounds on the same synthetic route. Specifically, the compounds on the synthetic route of compound X2a (pyrrole 8ad) are compounds in which the two alphabetical letters shown after the number are "ad."

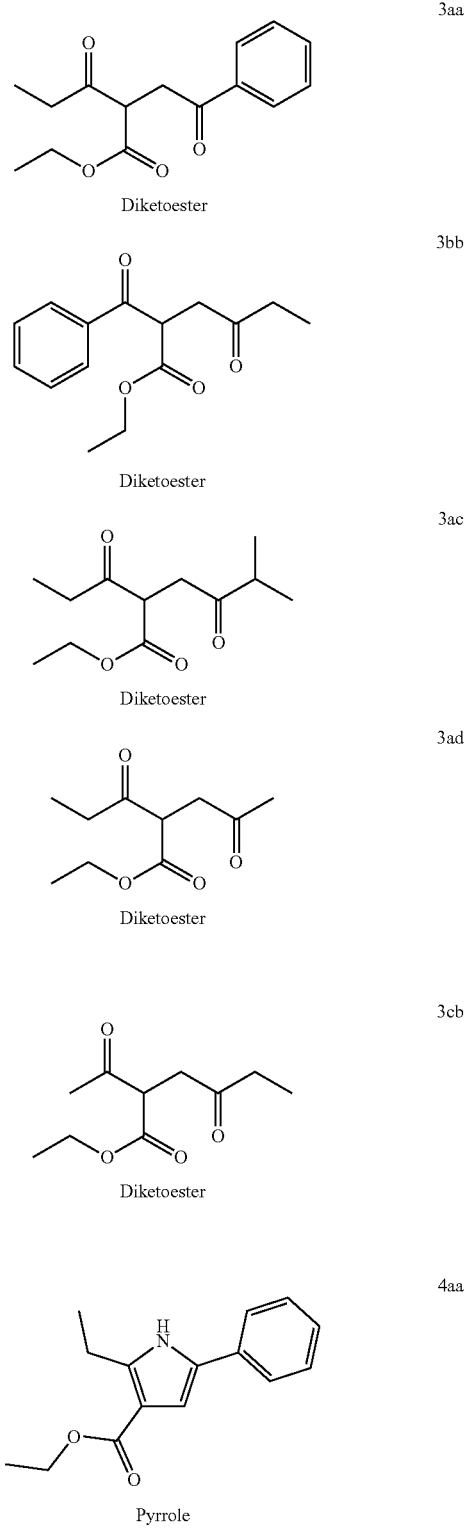

The specific structures of desired product 8 and compounds for obtaining the desired product (diketoester 3 and the like) are shown below. The numbers correspond to those in the above synthetic route. Compounds with the same two 4bb
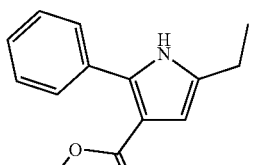
Pyrrole
4ac
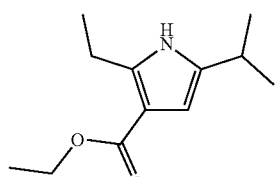
Pyrrole
4ad
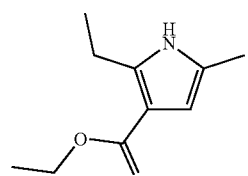
Pyrrole
4cb
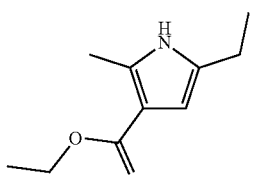
Pyrrole
5aa
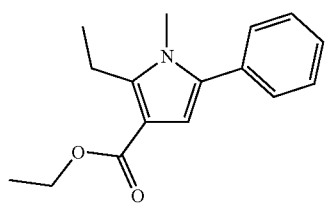
N-methylpyrrole
5bb
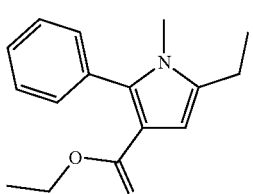
N-methylpyrrole
5ac
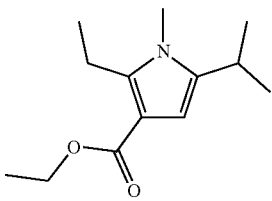
N-methylpyrrole
5ad
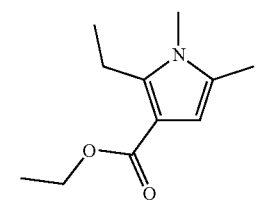
N-methylpyrrole
5cb
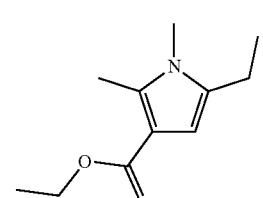
N-methylpyrrole
6aa
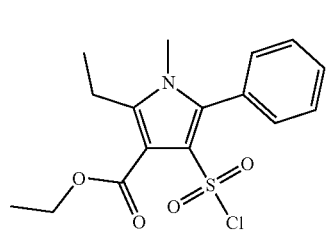
Sulfonic acid chloride
6bb
Sulfonic acid chloride
6ac
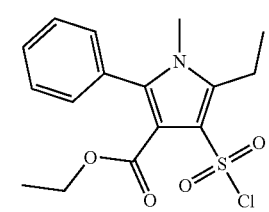
Sulfonic acid chloride

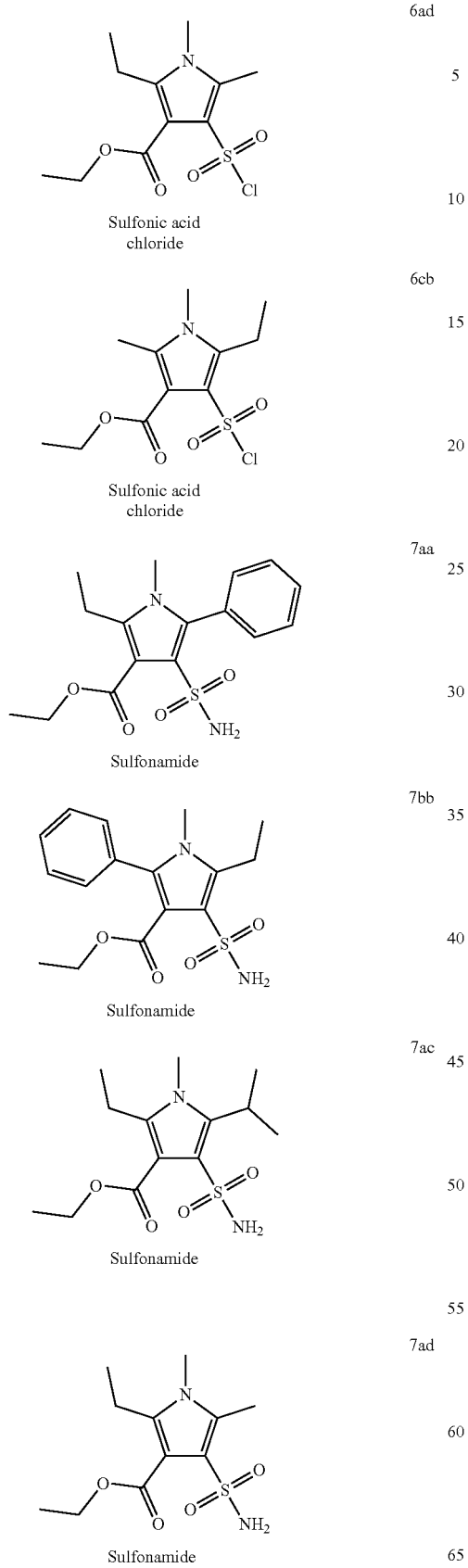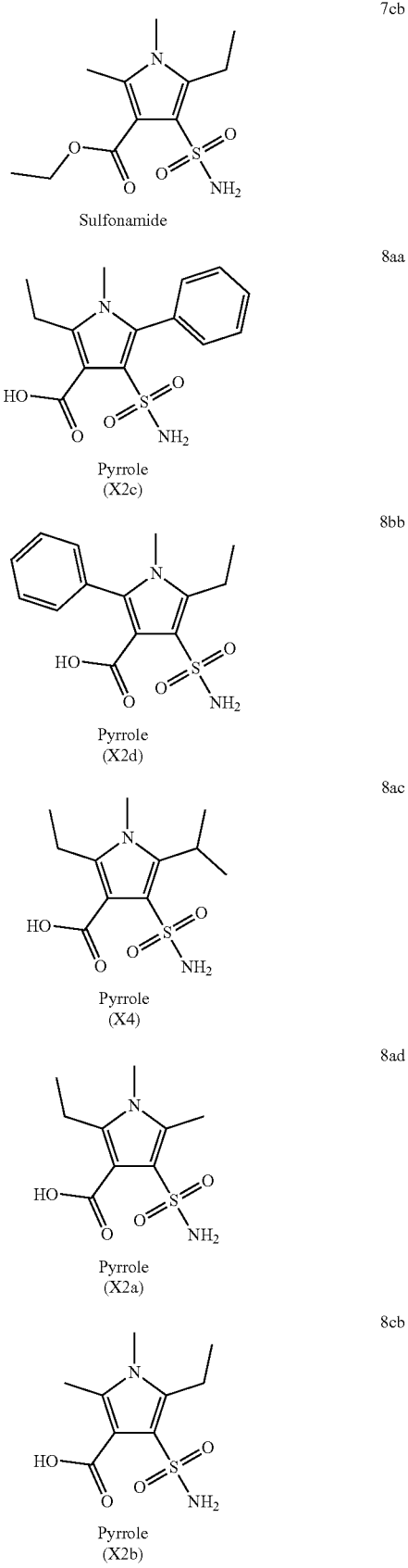

Synthesis Example 7-1

Synthesis of Compound X2a (Pyrrole 8ad)

The coupling of ethyl 3-oxovalerate 1a and bromoacetone 2d was performed to synthesize diketoester 3ad. Specifically, sodium hydride (60% in liquid paraffin, 960 mg, 24.00 mmol, 1.20 eq.) and THF (35 mL) were placed in a 50-mL three-necked flask equipped with a stir bar in a nitrogen atmosphere; and ice-cooled. Subsequently, ethyl 3-oxovalerate 1a (2.85 mL, 20.00 mmol) was added dropwise neat to the obtained gray suspension using a syringe. At this time, foaming was confirmed. After the mixture was further stirred in an ice bath for 30 minutes, a solution (15 mL) of bromoacetone 2d (3.00 g, 22.00 mmol, 1.10 eq.) in THF was quickly added. Further, after 1 hour, TLC analysis (UV, phosphomolybdic acid) confirmed the disappearance of compound 1a and the formation of a new spot (developing solvent: hexane/ethyl acetate=9/1, Rf value: 0.3). A saturated ammonium chloride aqueous solution and ethyl acetate were then added to the reaction mixture to stop the reaction. After separation of two layers, the aqueous layer was extracted with ethyl acetate, and the combined organic layers were washed with a saturated sodium chloride aqueous solution and dried over sodium sulfate. After the drying agent was filtered off, the filtrate was concentrated under reduced pressure to obtain 4.33 g of an orange, oily substance. The obtained crude product was purified by silica gel column chromatography (two times in total, using silica gels (1) and (2) (150 g each)). For elution, (1) hexane/ethyl acetate=9/1 (2 L)→1/1 (700 mL) and (2) hexane/ethyl acetate=4/1 (2 L) were used. A fraction of the desired product was concentrated to obtain 2.50 g (yield: 62%) of the desired diketoester 3ad as a light-yellow liquid.

Pyrrole 4ad was synthesized from diketoester 3ad by Paal-Knorr pyrrole synthesis. Specifically, diketoester 3ad (2.50 g, 12.49 mmol), ammonium acetate (9.63 g, 124.9 mmol, 10.00 eq.), and acetic acid (40 mL) were placed in a 100-mL one-necked flask equipped with a stir bar; and the mixture was stirred at 80° C. After 3 hours, TLC analysis (UV, phosphomolybdic acid) confirmed the disappearance of compound 3ad (hexane/ethyl acetate=4/1, Rf value: 0.3) and the formation of a new spot (Rf value: 0.4) above this compound. The reaction mixture was then allowed to cool to room temperature, and concentrated under reduced pressure. Subsequently, the obtained brown, oily substance was diluted with ethyl acetate and distilled water. After separation of two layers, the aqueous layer was extracted with ethyl acetate. The combined organic layers were washed with a saturated sodium chloride aqueous solution, and dried over sodium sulfate. The drying agent was filtered off, and the filtrate was concentrated under reduced pressure to obtain 2.11 g (yield: 93%) of the desired pyrrole 4ad as a brown liquid.

Pyrrole 4ad was alkylated with methyl iodide to synthesize N-methylpyrrole 5ad. Specifically, pyrrole 4ad (2.11 g, 11.63 mmol), methyl iodide (3.6 mL, 57.83 mmol, 4.97 eq.), and THF (45 mL) were placed in a 100-mL one-necked flask equipped with a stir bar; and ice-cooled. Subsequently, sodium hydride (60% in liquid paraffin, 698 mg, 17.44 mmol, 1.50 eq.) was added to the obtained brown solution, and foaming was confirmed. After 30 minutes, TLC analysis (UV, phosphomolybdic acid) showed that compound 4ad remained. Further, stirring was continued, and the disappearance was confirmed by TLC analysis after 62 hours. Distilled water was added to the reaction mixture to stop the reaction, followed by extraction with diethyl ether. The combined organic layers were washed with a saturated sodium chloride aqueous solution, and dried over sodium sulfate. The drying agent was filtered off, and the filtrate was concentrated under reduced pressure to obtain 2.80 g of a reddish-brown, oily substance. The obtained crude product was purified by silica gel column chromatography (using 50 g; diameter: 30 mm; height: 190 mm). As an eluent, hexane/ethyl acetate=9/1 (650 mL) was used. A fraction of the desired product was concentrated to obtain 1.72 g (yield: 76%) of N-methylpyrrole 5ad as a brown liquid.

N-methylpyrrole 5ad was chlorosulfonated to synthesize sulfonic acid chloride 6ad. Specifically, chlorosulfuric acid (5.9 mL, 88.76 mmol, 10.05 eq.) was placed in a 100-mL one-necked flask equipped with a stir bar that had been sufficiently purged with nitrogen, and was stirred in an ice bath (with caution in regards to smoke generation). After N-methylpyrrole 5ad (1.72 g, 8.83 mmol) was added portionwise thereto, the flask was sealed, and the mixture was allowed to warm to room temperature (brown, clear solution). After 1 hour and 30 minutes, TLC analysis (UV, phosphomolybdic acid) confirmed the disappearance of compound 5ad (developing solvent: hexane/ethyl acetate=9/1, Rf value: 0.7) and the formation of a new spot (Rf value: 0.35). The reaction mixture was ice-cooled, and slowly added dropwise to ice-cooled distilled water; and a light-brown solid was precipitated. The resulting solid was dissolved in methylene chloride. After separation of two layers, the aqueous layer was extracted with methylene chloride, and the combined organic layers were dried over sodium sulfate. The drying agent was filtered off, and the filtrate was concentrated under reduced pressure to obtain 1.75 g (yield: 68%) of sulfonic acid chloride 6ad as a brown solid.

Sulfonic acid chloride 6ad was reacted with an ammonia/dioxane solution to synthesize sulfonamide 7ad. Specifically, sulfonic acid chloride 6ad (1.75 g, 5.97 mmol) and a 0.5 M ammonia/dioxane solution (36.00 mL, 18.00 mmol, 3.01 eq.) were placed in a 100-mL one-necked flask equipped with a stir bar, and the mixture was stirred at room temperature. After 26 hours and 30 minutes, TLC analysis (UV, phosphomolybdic acid) confirmed the disappearance of compound 6ad (developing solvent: hexane/ethyl acetate=1/1, Rf value: 0.6) and the formation of a new spot (Rf value: 0.3). After concentration under reduced pressure, the resulting crude product was subjected to cake-washing with cold hexane/ethyl acetate=1/1, and the solid was collected and dried to obtain 1.50 g (yield: 92%) of the desired sulfonamide 7ad as a brown solid.

An ester of sulfonamide 7ad was hydrolyzed under basic conditions to synthesize desired pyrrole compound 8ad (X2a). Specifically, sulfonamide 7ad (Lot. 4188163, 1.41 g, 5.13 mmol) and a 2 M potassium hydroxide/ethanol solution (50.0 mL, 100.0 mmol, 19.48 eq.) were placed in a 100-mL one-necked flask equipped with a stir bar; and the mixture was stirred at 80° C. After 3 hours and 30 minutes, TLC analysis (UV, phosphomolybdic acid) confirmed the disappearance of compound 7ad (developing solvent: ethyl acetate only, Rf value: 0.75) and the formation of a new spot (Rf value: 0.5). The reaction mixture was allowed to cool to room temperature. Acetic acid (6 mL) was added, and the mixture was allowed to stand in a refrigerator. The next day, the precipitated crystals were filtered with a Kiriyama funnel, and subjected to cake-washing with distilled water (10 mL); and the solid was dissolved. Thus, concentration under reduced pressure was performed again, and the precipitated solid was subjected to cake-washing with distilled water (10 mL). The remaining solid was dried under reduced pressure at 50° C. to obtain 687 mg of a brown solid. The obtained brown solid was purified by silica gel column chromatography (using 157 g of silica gel). The eluent used was chloroform/methanol=9/1 (2.1 L)-4/1 (75 mL)→methanol only (300 mL). The polarity was increased to methanol alone here because the polarity of the desired product was high, and the yield was low in study 2.6.1. Each fraction was concentrated to obtain 112 mg of a low-polarity brown solid, and 504 mg of a high-polarity brown solid. A part of the obtained solids was diluted with deuterated DMSO, and $^1$H and $^{13}$C NMR measurement was performed. The results confirmed that the high-polarity brown solid was the desired pyrrole 8ad (X2a) (yield: 40%, HPLC purity: 98.5%).

$^1$H-NMR (400 MHz, DMSO_d$_6$): δ 1.06 (t, J=6.0 Hz, 3H), 2.42 (s, 3H), 2.94 (q, J=6.0 Hz, 2H), 3.42 (s, 3H), 3.5-9.0 (bs, 3H); $^{13}$C-NMR (100 MHz, DMSO_d$_6$): 11.0, 14.3, 30.5, 48.0, 108.9, 121.4, 130.5, 140.4, 168.0; MS Calcd.: 245.06; MS Found: 245.03 ([M−1]$^-$).

Synthesis Example 7-2

Synthesis of Compound X2b

Compound X2b was synthesized in a manner similar to that of Synthesis Example 7-1. Compound X2b was obtained as a light-brown solid (yield: 33%, HPLC purity: 95.9%).

$^1$H-NMR (400 MHz, DMSO_d$_6$): δ1.06 (t, J=6.0 Hz, 3H), 2.41 (s, $^3$H), 2.92 (q, J=6.0 Hz, 2H), 3.44 (s, 3H), 6.91 (bs, 2H, —SONH$_2$); $^{13}$C-NMR (100 MHz, DMSO-d$_6$): 11.4, 14.8, 17.3, 30.2, 109.8, 120.8, 135.1, 136.5, 165.4; MS Calcd.: 245.06; MS Found: 245.05 ([M−1]$^-$).

Synthesis Example 7-3

Synthesis of Compound X2c

Compound X2c was synthesized in a manner similar to that of Synthesis Example 7-1. Compound X2c was obtained as a light-brown solid (yield: 13%, HPLC purity: 96.0%).

$^1$H-NMR (400 MHz, DMSO-d$_6$): δ 1.16 (t, J=6.0 Hz, 3H), 2.95 (q, J=6.0 Hz, 2H), 3.24 (s, 3H), 6.84 (bs, 2H, —SONH$_2$), 12.8 (bs, 1H, —COOH); $^{13}$C-NMR (100 MHz, DMSO-d$_6$): 14.0, 18.1, 31.9, 108.6, 123.1, 128.1, 128.8, 131.3, 131.6, 135.1, 142.2, 166.6.; MS Calcd.: 307.08; MS Found: 307.09 ([M−1]$^-$).

Synthesis Example 7-4

Synthesis of Compound X2d

Compound X2d was synthesized in a manner similar to that of Synthesis Example 7-1. Compound X2d was obtained as a light-yellow solid (yield: 24%, HPLC purity: 99.3%).

$^1$H-NMR (400 MHz, DMSO_d$_6$): δ 1.14 (t, J=6.0 Hz, 3H), 2.98 (q, J=5.6 Hz, 2H), 3.27 (s, 3H), 7.10 (bs, 2H, —SONH$_2$), 7.32 (m, 2H), 7.41 (m, 3H), 12.3 (bs, 1H, —COOH); $^{13}$C-NMR (100 MHz, DMSO-d$_6$): 14.5, 31.8, 39.5, 121.3, 128.3, 128.4, 128.5, 131.1, 132.2, 136.7, 136.8, 160.0; MS Calcd.: 307.08; MS Found: 307.03 ([M−1]$^-$).

Synthesis Example 7-5

Synthesis of Compound X4

Compound X4 was synthesized in a manner similar to that of Synthesis Example 7-1. Compound X4 was obtained as a light-yellow solid (yield: 24%, HPLC purity: 87.5%).

$^1$H-NMR (400 MHz, DMSO_d$_6$): δ1.06 (t, J=6.0 Hz, 3H), 1.27 (d, J=6.0 Hz, 6H), 2.83 (q, J=6.0 Hz, 2H), 2.90 (m, 1H), 3.60 (s, 3H), 4.27 (bs, 1H, —COOH), 6.95 (bs, 2H, —SONH$_2$); MS Calcd.: 273.09; MS Found: 273.06 ([M−1]$^-$).

Synthesis Example 8

Synthesis of Compound X3a

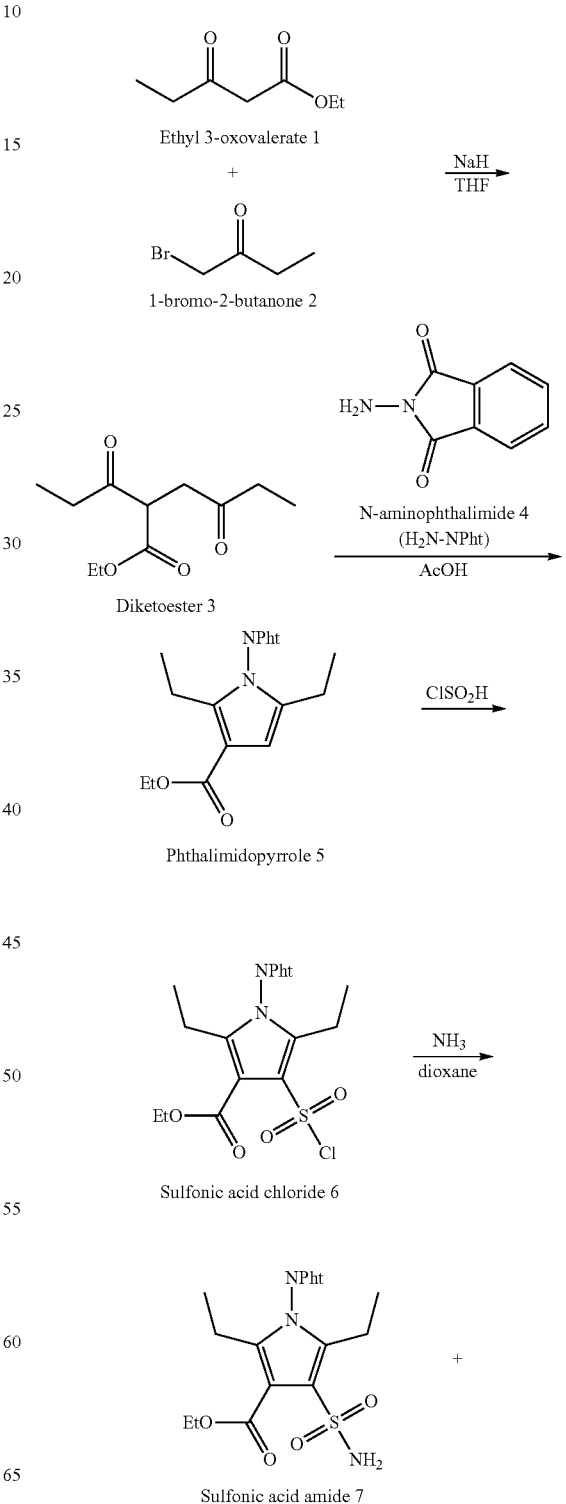

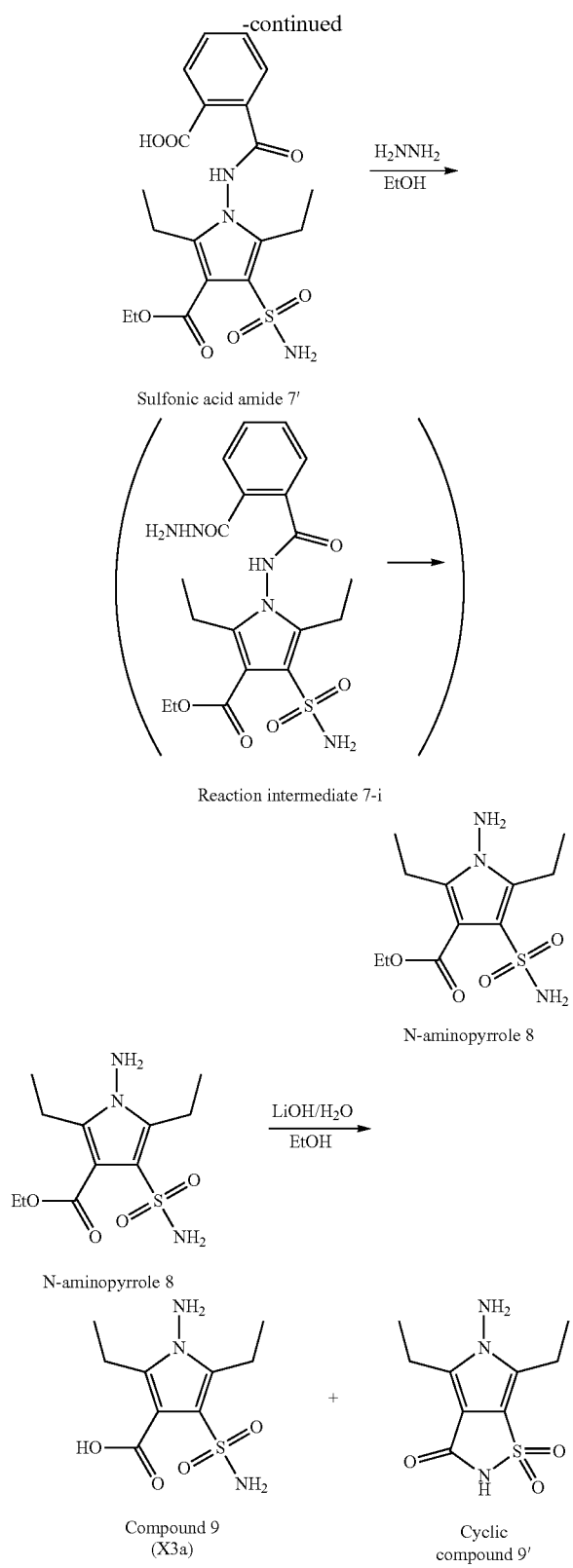

Compound X3a was synthesized according to the above reaction scheme. Specifically, compound X3a was synthesized as follows.

The coupling of ethyl 3-oxovalerate 1 and 1-bromo-2-butanone 2 was performed to synthesize diketoester 3.

Specifically, sodium hydride (60% in liquid paraffin, 139 mg, 3.48 mmol, 1.20 eq.) and THF (5.5 mL) were placed in a 30-mL two-necked recovery flask equipped with a thermometer and a stir bar in a nitrogen atmosphere, and ice-cooled. Subsequently, ethyl 3-oxovalerate 1 (418 mg, 2.90 mmol) was added dropwise to the obtained gray suspension. At this time, foaming and exotherm were confirmed (0.7° C.→12.5° C.). A solution (2.0 mL) of 1-bromo-2-butanone 2 (482 mg, 3.48 mmol, 1.10 eq.) in THF was added dropwise to the reaction liquid that had become a clear solution by stirring in an ice bath for 30 minutes, and stirring was continued in the ice bath. The reaction liquid turned from a clear solution to a white, turbid liquid. TLC analysis (UV, phosphomolybdic acid) 2 hours after dropwise addition confirmed the remainder of ethyl 3-oxovalerate 1 and a new spot (developing solvent: hexane/ethyl acetate=9/1, Rf value: 0.3). The reaction liquid was allowed to warm to room temperature, and further stirred for 2.5 hours. TLC analysis was performed in the same manner. The results showed that, from the spot density, the reaction appeared to proceed compared with before warming to room temperature; however, the disappearance of ethyl 3-oxovalerate 1 was not confirmed. After the reaction liquid was ice-cooled, a saturated ammonium chloride aqueous solution (20 mL) and ethyl acetate (20 mL) were added to stop the reaction (exothermic: 0.8° C.→15.7° C.). After separation of two layers, the aqueous layer was extracted with ethyl acetate (30 mL) twice, and the combined organic layers were washed with a saturated sodium chloride aqueous solution (40 mL) and dried over sodium sulfate. The drying agent was filtered off, and the filtrate was then concentrated under reduced pressure to obtain 894 mg of a yellow, oily substance. The obtained crude product was purified by using a medium-pressure preparative liquid chromatograph (silica gel) produced by Yamazen Corporation. The eluent used was ethyl acetate/hexane 0% (3 minutes, gradient: 10 minutes) →10% (27 minutes). A fraction of the desired product was concentrated and vacuum-dried at 40° C. for 1 hour to obtain 624 mg of diketoester 3 in which 22.3 mg (3.6 wt %) of compound 1 was mixed, as a colorless, clear liquid (weight of diketoester 3 in the mixture: 602 mg, yield: 97%).

Paal-Knorr pyrrole synthesis was performed using N-aminophthalimide 4 to synthesize phthalimidopyrrole 5. Specifically, diketoester 3 (Lot. 5187301, 602 mg, 2.81 mmol) and N-aminophthalimide 4 (455 mg, 2.81 mmol, 1.00 eq.) were placed in a 10-mL recovery flask equipped with a stir bar and a Dimroth condenser in a nitrogen atmosphere; and acetic acid (3.6 mL) was further added, followed by stirring at room temperature (N-aminophthalimide 4 was not dissolved). The oil bath temperature was set to about 130° C., and the reaction liquid was refluxed (N-aminophthalimide 4 was completely dissolved at a bath temperature of about 80° C.). After 1 hour, TLC analysis (UV, phosphomolybdic acid) confirmed the remainder of diketoester 3; and a new spot (developing solvent: hexane/ethyl acetate=4/1, Rf value: 0.3). After reflux for another 3 hours, TLC analysis was performed in the same manner, and the results showed that diketoester 3 still remained. N-aminophthalimide 4 (91.1 mg, 0.56 mmol, 0.2 eq.) was added, followed by reflux for 30 minutes. Thereafter, TLC analysis showed that the spot of diketoester 3 became fainter, and reflux was further performed for 18 hours. Although TLC analysis (UV, phosphomolybdic acid) of the reaction liquid confirmed the remainder of diketoester 3 very weakly, the heating was stopped to stop the reaction. Acetic acid was distilled off under reduced pressure; and ethyl acetate (40 mL) and distilled water (30 mL) were added, followed by stirring for 5 minutes. After separation of two layers, the aqueous layer was extracted with ethyl acetate (30 mL), and the combined organic layers were washed with a saturated sodium hydrogencarbonate aqueous solution (40 mL). The pH was adjusted to about 9 using pH test paper. Washing was performed with a saturated sodium chloride aqueous solution (30 mL), followed by drying over sodium sulfate. The drying agent was filtered off, and the filtrate was then concentrated under reduced pressure to obtain 1.01 g of a yellow solid. The obtained crude product was purified by using a medium-pressure preparative liquid chromatograph (silica gel) produced by Yamazen Corporation. The eluent used was ethyl acetate/hexane 0% (3 minutes, gradient: 10 minutes)→10% (3 minutes, gradient: 10 minutes)→20% (16 minutes). A fraction of the desired product was concentrated and vacuum-dried at 40° C. for 1 hour to obtain 596 mg of phthalimidopyrrole 5 as white crystals (yield: 62%).

Chlorosulfonation was performed using chlorosulfuric acid to synthesize sulfonic acid chloride 6. Specifically, chlorosulfuric acid (1.1 mL, 16.55 mmol, 10.09 eq.) was placed in a 10-mL screw-top test tube equipped with a stir bar that had been sufficiently purged with nitrogen, and was stirred in an ice bath (with caution in regards to smoke generation). After phthalimidopyrrole 5 (Lot. 5188011, 596 mg, 1.75 mmol) was added portionwise thereto, the tube was sealed, and the mixture was allowed to warm to room temperature (orange clear solution). After 17 hours, TLC analysis (UV, phosphomolybdic acid) confirmed the disappearance of phthalimidopyrrole 5; and a new spot (developing solvent: hexane/ethyl acetate=4/1, Rf value: 0.2). Moreover, a small amount of the reaction liquid was taken and subjected to 1H NMR measurement with deuterated chloroform, and the disappearance of the pyrrole ring proton was confirmed (brown solution). The reaction liquid was slowly added dropwise to ice-cooled distilled water (40 mL) to stop the reaction. After the aqueous layer was extracted with methylene chloride (40 mL) twice, the combined organic layers were dried over sodium sulfate. The drying agent was filtered off, and the filtrate was then concentrated under reduced pressure to obtain a light-brown, oily substance. Vacuum-drying was performed at 40° C. for 1 hour to obtain 410 mg of sulfonic acid chloride 6 as light-brown amorphous crystals (yield 72%).

The obtained sulfonic acid chloride 6 was reacted with an ammonia/dioxane solution to synthesize sulfonic acid amide 7. Specifically, sulfonic acid chloride 6 (Lot. 5187201, 369.3 mg, 0.84 mmol) was placed in a 30-mL recovery flask equipped with a stir bar; and a 0.5 M ammonia/dioxane solution (7.3 mL, 3.64 mmol, 4.32 eq.) was added under an ice bath, followed by stirring at room temperature. After 4 hours, TLC analysis (UV, phosphomolybdic acid) confirmed two new spots (developing solvent: hexane/ethyl acetate=1/1, Rf values: 0.4 and 0.02). The ammonia/dioxane solution was distilled off under reduced pressure, and the obtained crude product was purified by using a medium-pressure preparative liquid chromatograph (silica gel) produced by Yamazen Corporation. The eluent used was ethyl acetate/hexane 55% (3 minutes, gradient: 10 minutes)→76% (3 minutes, gradient: 13 minutes)→100% (11 minutes). No fraction that appeared to be the desired product was obtained. Instead, a fraction that was mainly obtained was concentrated and vacuum-dried at 40° C. for 1 hour to obtain 68.0 mg (yield: 19%) of sulfonic acid amide 7 and 170 mg (yield: 46%) of sulfonic acid amide 7', both as white amorphous crystals.

Sulfonic acid amide 7 and sulfonic acid amide 7' were reacted with hydrazine to synthesize N-aminopyrrole 8. Specifically, sulfonic acid amide 7 and sulfonic acid amide 7' (Lot. 5188232, 295 mg in total, 0.68 mmol (all calculated as 7')) were placed in a 30-mL recovery flask equipped with a stir bar and a condenser; and ethanol (2.4 mL) was added, followed by stirring. After hydrazine monohydrate (d=1.03) (328 µL, 6.75 mmol, 10.0 eq.) was added at room temperature, the mixture was heated to 100° C., and stirred. After 1 hour, TLC analysis (UV, phosphomolybdic acid) confirmed the disappearance of sulfonic acid amide 7, sulfonic acid amide 7', and the reaction intermediate, and the formation of two new spots (developing solvent: hexane/ethyl acetate=1/1, Rf values: 0.5 and 0.03). The reaction liquid was distilled off under reduced pressure, and the obtained crude product was purified by using a medium-pressure preparative liquid chromatograph (silica gel) produced by Yamazen Corporation. At the time of charging, the crude product was dissolved using DMSO. The eluent used was ethyl acetate/hexane 0% (16 minutes, gradient: 13 minutes)→55% (7 minutes). The obtained fraction was concentrated and vacuum-dried at 40° C. for 1 hour to obtain a DMSO solution of N-aminopyrrole 8. Further, the DMSO solution was passed through a medium-pressure preparative liquid chromatograph (produced by Yamazen Corporation) having an injection column attached thereto (eluent: ethyl acetate/hexane 50% (3 minutes, gradient: 13 minutes)→1000 (17 minutes)), and DMSO was removed to obtain 128 mg of N-aminopyrrole 8 as white crystals (yield: 65%).

N-aminopyrrole 8 was reacted with 2 M LiOH/$H_2O$ to synthesize compound 9 (X3a). Specifically, N-aminopyrrole 8 (Lot. 5189181, 96 mg, 0.33 mmol) was placed in a 10-mL screw-top test tube equipped with a stir bar. 2 M LiOH/$H_2O$ (717 µL, 1.433 mmol, 4.32 eq.) and ethanol (143 µL) were added, and the mixture was stirred at 100° C. After 1 hour, HPLC analysis confirmed the disappearance of N-aminopyrrole 8. After the reaction liquid was cooled to room temperature, the pH was adjusted to about 4 to 4.5 with 1 M hydrochloric acid to produce a white precipitate. The reaction liquid was transferred to a 50-mL recovery flask, and concentrated under reduced pressure (light-yellow solid). Methanol (1 mL) was added in the system, and the solid was completely dissolved by ultrasonic treatment. After chloroform (19 mL) was added, the solution was allowed to stand in a freezer (about −10° C.) overnight. The precipitated solid was collected by suction filtration (10.1 mg). The mother liquor was concentrated under reduced pressure. The combined crude product was purified by using a medium-pressure preparative liquid chromatograph produced by Yamazen Corporation (eluent: methanol/chloroform 10% (5 minutes, gradient: 5 minutes)→25% (15 minutes)). The fractions in which compound 9 was eluted were combined, concentrated under reduced pressure, and dried under reduced pressure at 50° C. for 2 hours to obtain compound 9 as a light-yellow solid (yield: 51%). $^1$H-NMR (400 MHz, DMSO-$d_6$): δ 1.09 (t, J=6.0 Hz, 3H), 1.09 (t, J=7.2 Hz, 3H), 2.91-2.98 (m, 4H), 5.64 (bs, 2H, —N—$NH_2$), 7.24 (bs, 2H, —$SONH_2$). $^{13}$C-NMR (100 MHz, DMSO-$d_6$): δ 1.09.

Synthesis Example 9

Synthesis of Compound X3b

Compound X3b can be synthesized as follows.

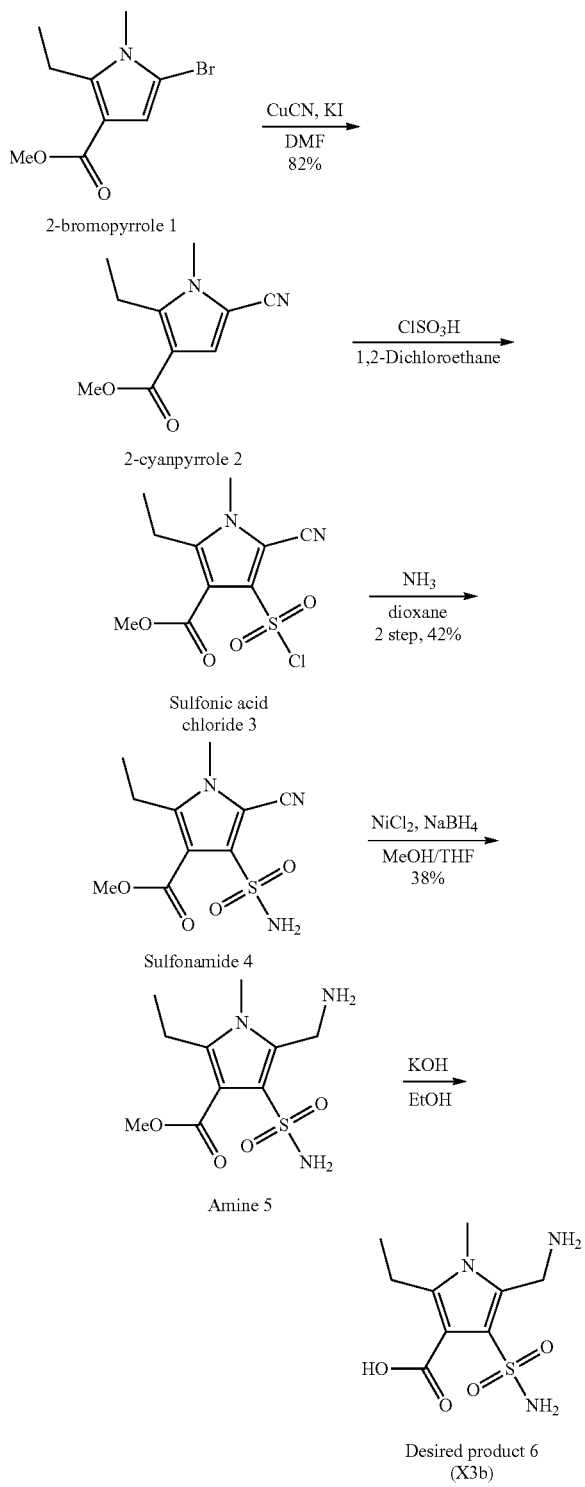

2-bromopyrrole 1 (3.9 g, 15.85 mmol) and DMF (95 mL) were placed in a 500-mL three-necked recovery flask equipped with a stir bar, and the mixture was stirred at room temperature. Copper cyanide (I) (7.1 g, 79.24 mmol, 5.0 eq.) and potassium iodide (184 mg, 1.11 mmol, 0.07 eq.) were added thereto, and the mixture was stirred at 120° C. Stirring was performed for 17 hours. After completion of the reaction, dilution was performed with ethyl acetate (95 mL). Thereafter, distilled water (95 mL) was added, and the solid was filtered off by filtration with Celite. After the filtrate was partitioned, the aqueous layer was extracted with ethyl acetate (100 mL). The organic layers were combined and washed with a 5% sodium chloride aqueous solution (300 mL) three times. The organic layers were dried over sodium sulfate. The drying agent was filtered off, and the filtrate was then concentrated under reduced pressure to obtain 3.12 g of a brown, oily crude product. The obtained crude product was purified by using a medium-pressure preparative liquid chromatograph (silica gel) produced by Yamazen Corporation. The eluent used was ethyl acetate/hexane 10% (3 minutes, gradient: 10 minutes→31%, 14 minutes). A fraction was concentrated to obtain 2-cyanopyrrole 2 (2.49 g, 82%) as a light-yellow solid.

1,2-dichloroethane (42 mL) and chlorosulfuric acid (7.23 mL, 12.73 mmol, 10.0 eq.) were placed in a 300-mL recovery flask equipped with a stir bar in an ice bath, and the mixture was stirred in the ice bath. A solution of 2-cyanopyrrole 2 (2.1 g, 10.93 mmol) in 1,2-dichloroethane (13 mL) was added dropwise thereto, and the mixture was stirred at room temperature for 40 minutes. After completion of the reaction, phosphorus pentachloride (11.38 g, 54.63 mmol, 5.0 eq.) was added to the reaction liquid under ice-cooling, and the mixture was heated with stirring at 60° C. for 1 hour. After the reaction liquid was cooled to room temperature, the reaction liquid was added dropwise to ice-cooled distilled water (200 mL) to stop the reaction. After partition, the aqueous layer was extracted with 200 mL of dichloromethane, and the organic layers were combined and dried over sodium sulfate. The drying agent was filtered off, and the filtrate was then concentrated under reduced pressure to obtain a crude product of sulfonic acid chloride 3 (3.41 g, crude yield: 107%) as an orange oil.

A 0.5 M ammonia/dioxane solution (101 mL, 50.67 mmol, 4.32 eq.) was added to the crude product of sulfonic acid chloride 3 (3.41 g, 11.73 mmol) in a 300-mL recovery flask equipped with a stir bar under ice-cooling, and the mixture was stirred at room temperature for 15 hours. After completion of the reaction, the insoluble matter was removed by filtration to obtain sulfonamide 4 (1.32 g, 42%) as an off-white solid.

Sulfonamide 4 (933 mg, 3.442 mmol), nickel chloride (II) (446.0 mg, 0.369 mmol, 1.0 eq.), methanol (177 mL), and THF (177 mL) were placed in a 1000-mL recovery flask equipped with a stir bar, and the mixture was stirred at room temperature. Sodium borohydride (390.6 mg, 10.32 mmol, 3.0 eq.) was added thereto, and the mixture was stirred at room temperature. After 30 minutes, sodium borohydride (390.6 mg, 10.32 mmol, 3.0 eq.) was further added, and the mixture was stirred at room temperature. After 1 hour, nickel chloride (II) (446.0 mg, 0.369 mmol, 1.0 eq.) and sodium borohydride (390.6 mg, 10.32 mmol, 3.0 eq.) were further added, and the mixture was stirred at room temperature for 5 hours. Distilled water (100 mL) was added to stop the reaction. The insoluble matter was filtered off by suction filtration. The filtrate was concentrated under reduced pressure to obtain a crude product as a white solid. The obtained crude product was purified by using a medium-pressure preparative liquid chromatograph (eluent: methanol/chloroform 4% (3 minutes, gradient: 10 minutes)→110 (13 minutes)→30% (18 minutes)) to obtain amine 5 (355.6 mg, yield: 38%) as a light-yellow solid.

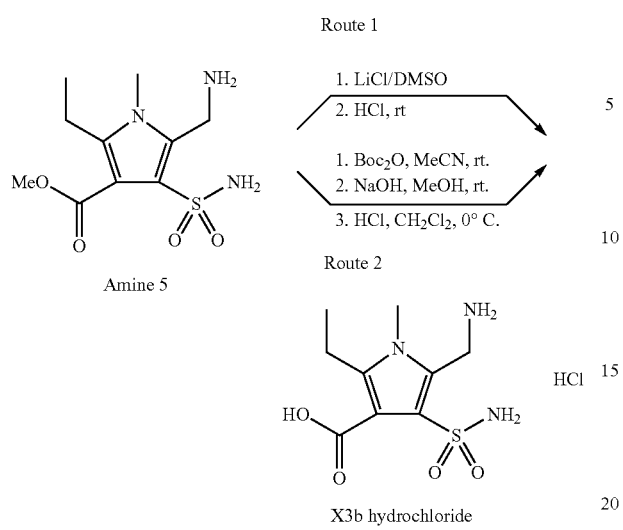

In the conversion of amine 5 to X3b, it is known that a cyclization reaction of a free amino group with sulfonamide is prioritized under common basic conditions. Thus, a Krapcho reaction, in which heating is performed together with lithium chloride in DMSO to convert the methyl ester to a carboxylic acid under neutral conditions, is useful (route 1). X3b is also obtained by introducing a t-butoxycarbonyl group (Boc group) into free amine 5, hydrolyzing the methyl ester, and deprotecting the Boc group under acidic conditions (route 2). In both cases, X3b can be successfully synthesized by ultimately obtaining hydrochloride.

4. Compound Analysis 2

Test Example 9

Enzyme Activity Measurement Test

A metallo-β-lactamase (IMP-1) (final concentration: 10 nM), and imipenem (final concentration: 100 μM) as a substrate were used. The imipenem decomposition activity (Dabs/min) at each point under the conditions of absorbance: 298 nm and temperature: 30° C. was measured by varying the concentrations of test substances (compounds Nos. 9-7, 9-8, and 9-9) as inhibitors (0 μM, 10 μM, and 100 μM). The activity when no test substance was added was defined as 100%, and the relative activity value when each test substance was individually added was calculated.

Table 3 shows the results. In Table 3, the leftmost column indicates the test substances as inhibitors.

TABLE 3

| | IMP-1 enzyme activity (%) | | |
|---|---|---|---|
| | No inhibitor | Inhibitor (10 μM) | Inhibitor (100 μM) |
| No. 9-7 | 100 | 100 | 35 |
| No. 9-8 | 100 | 89 | 45 |
| No. 9-9 | 100 | 104 | 37 |

As shown in Table 3, the addition of compound No. 9-7, compound No. 9-8, and compound No. 9-9 each individually inhibits β-lactamase activity.

Test Example 10

Drug Susceptibility Test 5

The test was performed in the same manner as in Test Example 1, except that X2a, X2b, X2c, X2d, X3a, and X4 were used as test substances (inhibitors). The inhibitor concentration was 10 μg/mL.

Table 4 shows the results. In Table 4, the leftmost column indicates the test substances as inhibitors.

TABLE 4

| | Meropenem MIC (μg/mL) IMP1-producing strain | Meropenem MIC (μg/mL) NDM-1-producing strain | Ceftazidime MIC (μg/mL) VIM-2-producing strain |
|---|---|---|---|
| No inhibitor | 2 | 4 | 16 |
| X2a | 0.031 | 0.0625 | 1 |
| X2b | 0.031 | 0.0625 | 1 |
| X2c | 0.031 | 0.5 | 1 |
| X2d | 0.031 | 0.0625 | 1 |
| X3a | 0.031 | 0.5 | 4 |
| X4 | 0.031 | 0.5 | 1 |

As shown in Table 4, the addition of compounds X2a, X2b, X2c, X2d, X3a, and X4 each individually decreases the MICs of the antimicrobial drugs against the β-lactamase-producing bacteria.

Test Example 11

Inhibition Constant (Ki) Measurement Test 2

The test was performed in the same manner as in Test Example 6, except that X2a, X2b, X2c, X2d, X3a, and X4 were used as test substances (inhibitors).

Table 5 shows the results. In Table 5, the leftmost column indicates the test substances as inhibitors.

TABLE 5

| | Enzymatic Inhibition Effect Ki (μM) | | |
|---|---|---|---|
| | IMP-1 | NDM-1 | VIM-2 |
| X2a | 1.77 | 1.83 | 0.023 |
| X2b | 0.98 | 1.73 | 0.1 |
| X2c | 1.24 | 1.5 | 0.019 |
| X2d | 0.11 | 0.08 | 0.033 |
| X3a | 21.4 | 22.1 | 1.97 |
| X4 | 0.9 | 4.3 | 0.017 |

As shown in Table 5, the addition of compounds X2a, X2b, X2c, X2d, X3a, and X4 each individually inhibits β-lactamase activity.

Test Example 12

Animal Study (Mouse Abdominal Infection Model) 1

After mice were infected with a laboratory strain (a strain of Escherichia coli in which a plasmid encoding a class B β-lactamase (IMP-1) was introduced), a test substance (compound A) was administered; and survival was observed. Specifically, the animal study was performed as follows.

The laboratory strain grown overnight on a Mueller-Hinton agar medium was scraped with a sterile swab, suspended in physiological saline, adjusted to 2-5×10$^8$ CFU/mL, and mixed with an equal amount of a 10% mucin solution (1-2.5×10$^8$ CFU/mL) to prepare a bacterial liquid. Mice (Crl:CD$_1$(ICR), male, 4 weeks old (Charles River Laboratories Japan, Inc.)) acclimated for 4 days after arrival were weighed, and then infected by intraperitoneal administration of 250 μL of the prepared bacterial liquid per mouse. An antimicrobial drug (meropenem trihydrate (WAKO 137-15674)) and the test substance were dissolved in physiological saline. A first intraperitoneal administration of the antimicrobial drug (0.2 mg/kg) and/or the test substance (100 mg/kg) was performed 1 hour after infection. A second administration was performed 3 hours after infection, in the same manner as the first administration (up to this point, day 0). From the next day (day 1), survival was observed at a fixed time daily, and the survival rate was recorded.

Figure 10:
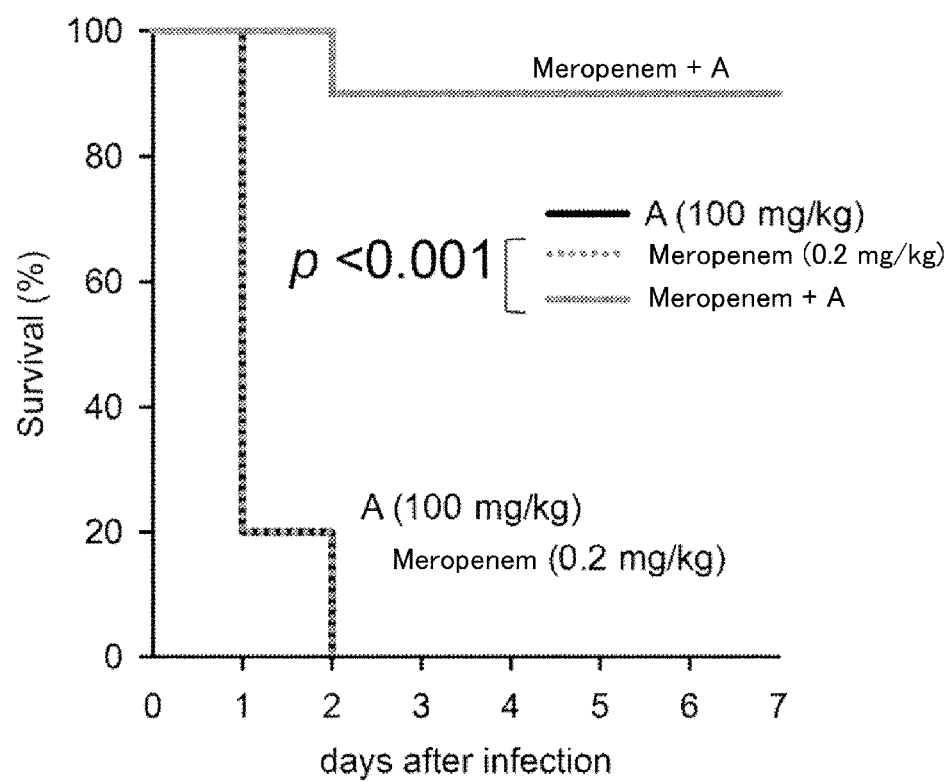
FIG. 10 shows the results of the animal study of Test Example 12. The vertical axis shows the survival rate, and the horizontal axis shows the number of days elapsed after infection with a laboratory strain (β-lactamase expression strain). A indicates a test substance (compound T).

FIG. 10 shows the results. The results revealed that the survival rate was notably improved by administering compound A.

Test Example 13

Animal Study (Mouse Abdominal Infection Model) 2

The animal study was performed in the same manner as in Test Example 12, except that in addition to a strain of *Escherichia coli* in which a plasmid encoding a class B lactamase (IMP-1) was introduced, bacteria (*K. pneumoniae*) in which a plasmid encoding NDM and VIM was introduced were used as a laboratory strain, compound I was administered as a test substance, the dosage of the antimicrobial drug was 0.8 mg/kg or 4 mg/kg, and the dosage of the test substance was 10 mg/kg.

Figure 11:
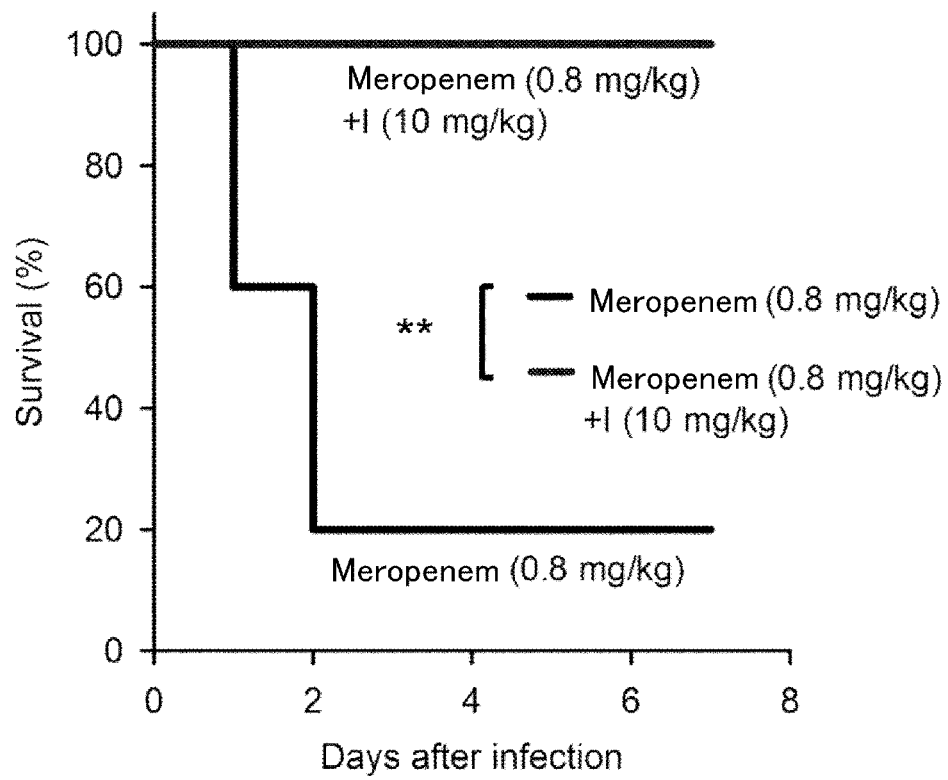
FIG. 11 shows the results of the animal study of Test Example 13 when a strain of *Escherichia coli* in which a plasmid encoding IMP-1 was introduced was used as a laboratory strain. The vertical axis shows the survival rate, and the horizontal axis shows the number of days elapsed after infection with the laboratory strain (β-lactamase expression strain). I indicates a test substance (compound I).
Figure 12:
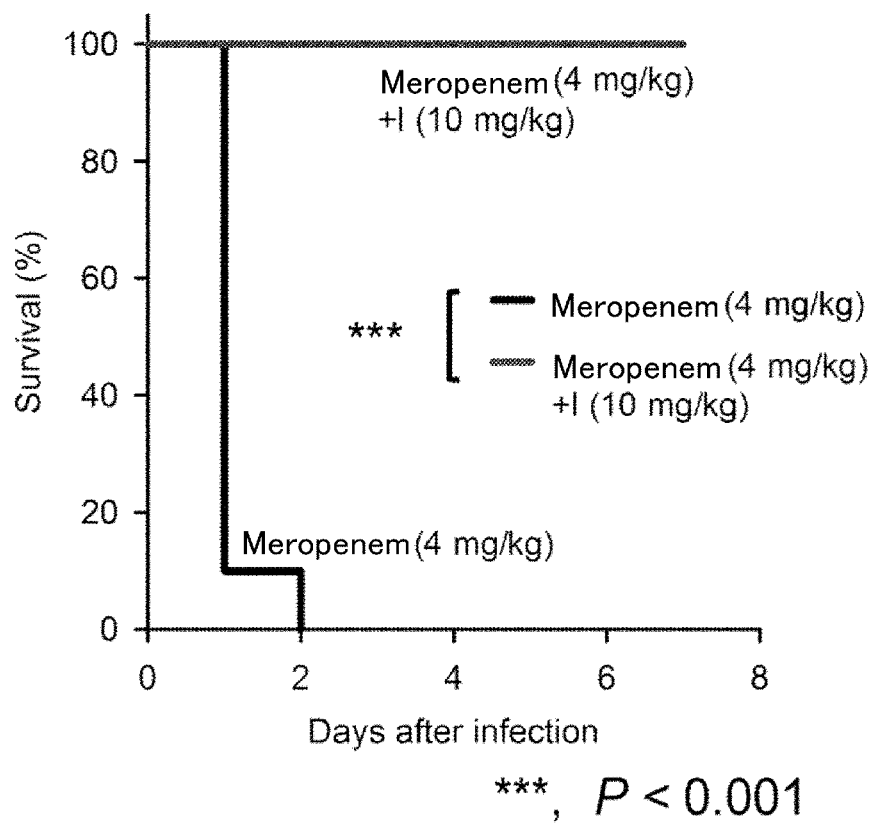
FIG. 12 shows the results of the animal study of Test Example 13 when bacteria (*K. pneumoniae*) in which a plasmid encoding NDM and VIM was introduced were used as a laboratory strain. The vertical axis shows the survival rate, and the horizontal axis shows the number of days elapsed after infection with the laboratory strain (β-lactamase expression strain). I indicates a test substance (compound I).

FIGS. 11 and 12 show the results. The results revealed that the survival rate was notably improved by administering compound I.

Test Example 14

Animal Study (Mouse Abdominal Infection Model) 3

The animal study was performed in the same manner as in Test Example 12, except that bacteria (*K. pneumoniae*) in which a plasmid encoding NDM and VIM was introduced were used as a laboratory strain, compound X2d was administered as a test substance, the dosage of the antimicrobial drug was 2 mg/kg or 8 mg/kg, and the dosage of the test substance was 10 mg/kg.

Figure 13:
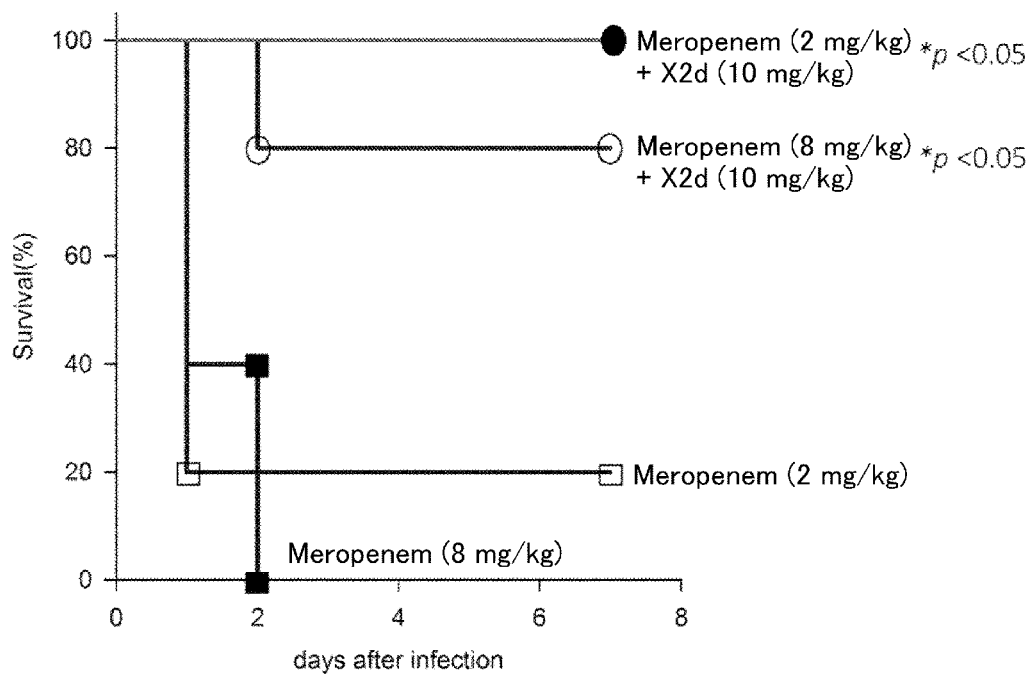
FIG. 13 shows the results of the animal study of Test Example 14. The vertical axis shows the survival rate, and the horizontal axis shows the number of days elapsed after infection with a laboratory strain (β-lactamase expression strain). X2d indicates a test substance (compound X2d).

FIG. 13 shows the results. The results revealed that the survival rate was notably improved by administering compound X2d.

The invention claimed is:

1. A β-lactamase inhibitor comprising a compound represented by formula (1) or a salt, hydrate, or solvate thereof,

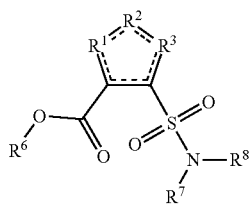

(1)

wherein
$R^1$ represents —C(—$R^4$)—;
$R^2$ represents —N(—$R^B$)$_n$—, —O—, or —C(—$R^4$)—;
$R^3$ represents —C(—$R^4$)— when $R^2$ is —N(—$R^B$)$_n$— or —O—, or represents —S— when $R^2$ is —C(—$R^4$)—;

each $R^4$ is the same or different and represents a hydrogen atom, a halogen atom, or a hydrocarbon group optionally substituted with one or more amino groups;
$R^B$ represents a hydrogen atom, a halogen atom, an optionally substituted amino group, or a hydrocarbon group optionally substituted with one or more amino groups;
n represents 0 or 1;
$R^6$ represents a hydrogen atom or a hydrocarbon group;
$R^7$ and $R^8$ are the same or different and each represents a hydrogen atom or a hydrocarbon group, or $R^7$ and $R^8$ are bonded to each other to form a ring with the adjacent nitrogen atom; and
a bond represented by a double line composed of a solid line and a dotted line is a single bond or a double bond.

2. The inhibitor according to claim 1, wherein the β-lactamase is a class B β-lactamase.

3. The inhibitor according to claim 1, wherein the β-lactamase is a class B1 β-lactamase.

4. An enhancer of an antimicrobial effect of a β-lactam antimicrobial compound, the enhancer comprising a compound represented by formula (1) or a salt, hydrate, or solvate thereof,

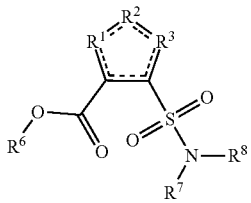

(1)

wherein
$R^1$ represents —C(—$R^4$)—;
$R^2$ represents —N(—$R^B$)$_n$—, —O—, or —C(—$R^4$)—;
$R^3$ represents —C(—$R^4$)— when $R^2$ is —N(—$R^B$)$_n$— or —O—, or represents —S— when $R^2$ is —C(—$R^4$)—;
each $R^4$ is the same or different and represents a hydrogen atom, a halogen atom, or a hydrocarbon group optionally substituted with one or more amino groups;
$R^B$ represents a hydrogen atom, a halogen atom, an optionally substituted amino group, or a hydrocarbon group optionally substituted with one or more amino groups;
n represents 0 or 1;
$R^6$ represents a hydrogen atom or a hydrocarbon group;
$R^7$ and $R^8$ are the same or different and each represents a hydrogen atom or a hydrocarbon group, or $R^7$ and $R^8$ are bonded to each other to form a ring with the adjacent nitrogen atom; and
a bond represented by a double line composed of a solid line and a dotted line is a single bond or a double bond.

5. An antimicrobial agent comprising a compound represented by formula (1) or a salt, hydrate, or solvate thereof, and a β-lactam antimicrobial compound, (1)

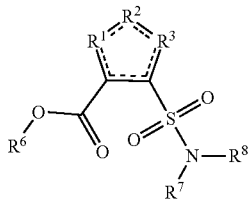

wherein
$R^1$ represents —C(—$R^A$)—;
$R^2$ represents —N(—$R^B$)$_n$—, —O—, or —C(—$R^A$)—;
$R^3$ represents —C(—$R^A$)— when $R^2$ is —N(—$R^B$)$_n$— or —O—, or represents —S— when $R^2$ is —C(—$R^A$)—;
each $R^A$ is the same or different and represents a hydrogen atom, a halogen atom, or a hydrocarbon group optionally substituted with one or more amino groups;
$R^B$ represents a hydrogen atom, a halogen atom, an optionally substituted amino group, or a hydrocarbon group optionally substituted with one or more amino groups;
n represents 0 or 1;
$R^6$ represents a hydrogen atom or a hydrocarbon group;
$R^7$ and $R^8$ are the same or different and each represents a hydrogen atom or a hydrocarbon group, or $R^7$ and $R^8$ are bonded to each other to form a ring with the adjacent nitrogen atom; and
a bond represented by a double line composed of a solid line and a dotted line is a single bond or a double bond.

6. An antimicrobial agent comprising a β-lactam antimicrobial compound, the antimicrobial agent being for use in administration in combination with a compound represented by formula (1) or a salt, hydrate, or solvate thereof, (1)

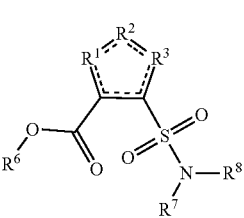

wherein
$R^1$ represents —C(—$R^A$)—;
$R^2$ represents —N(—$R^B$)$_n$—, —O—, or —C(—$R^A$)—;
$R^3$ represents —C(—$R^A$)— when $R^2$ is —N(—$R^B$)$_n$— or —O—, or represents —S— when $R^2$ is —C(—$R^A$)—;
each $R^A$ is the same or different and represents a hydrogen atom, a halogen atom, or a hydrocarbon group optionally substituted with one or more amino groups;
$R^B$ represents a hydrogen atom, a halogen atom, an optionally substituted amino group, or a hydrocarbon group optionally substituted with one or more amino groups;

n represents 0 or 1;
$R^6$ represents a hydrogen atom or a hydrocarbon group;
$R^7$ and $R^8$ are the same or different and each represents a hydrogen atom or a hydrocarbon group, or $R^7$ and $R^8$ are bonded to each other to form a ring with the adjacent nitrogen atom; and
a bond represented by a double line composed of a solid line and a dotted line is a single bond or a double bond.

7. A compound represented by formula (1A) or a salt, hydrate, or solvate thereof, (1A)

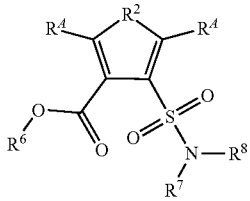

wherein
$R^2$ represents —N(—$R^B$)— or —O—;
each $R^A$ is the same or different and represents a hydrogen atom, a linear or branched alkyl group optionally substituted with one or more amino groups (with the proviso that when $R^2$ is —N(—$R^B$)—, the alkyl group has 1 to 5 carbon atoms, and when $R^2$ is —O—, the alkyl group has 2 to 5 carbon atoms), a $C_{3-7}$ cyclic alkyl group optionally substituted with one or more amino groups, or a phenyl group optionally substituted with one or more amino groups;
$R^B$ represents a hydrogen atom, an amino group optionally substituted with one or more linear or branched alkyl groups, or an alkyl group optionally substituted with one or more amino groups;
$R^6$ represents a hydrogen atom; and
$R^7$ and $R^8$ are the same or different and each represents a hydrogen atom or an alkyl group (with the proviso that the case in which both $R^7$ and $R^8$ are alkyl groups is excluded), or $R^7$ and $R^8$ are bonded to each other to form a ring with the adjacent nitrogen atom.

8. The compound or a salt, hydrate, or solvate thereof according to claim 7, wherein the alkyl group represented by $R^B$ is a $C_{1-4}$ linear alkyl group.

9. A medicament comprising the compound or a salt, hydrate, or solvate thereof according to claim 7.

10. A reagent comprising the compound or a salt, hydrate, or solvate thereof according to claim 7.

11. The inhibitor according to claim 2, wherein the β-lactamase is a class B1 β-lactamase.

12. A medicament comprising the compound or a salt, hydrate, or solvate thereof according to claim 8.

13. A reagent comprising the compound or a salt, hydrate, or solvate thereof according to claim 8.

* * * * *